United States Patent
Kondis et al.

(10) Patent No.: US 10,932,864 B2
(45) Date of Patent: Mar. 2, 2021

(54) TRACKING-BASED ILLUMINATION CONTROL SYSTEM

(71) Applicant: RxSight, Inc., Aliso Viejo, CA (US)

(72) Inventors: John Kondis, Irvine, CA (US); Ilya Goldshleger, Ladera Ranch, CA (US); Ronald M. Kurtz, Irvine, CA (US)

(73) Assignee: RxSight, Inc., Aliso Viejo, CA (US)

( * ) Notice: Subject to any disclaimer, the term of this patent is extended or adjusted under 35 U.S.C. 154(b) by 122 days.

(21) Appl. No.: 16/202,099

(22) Filed: Nov. 28, 2018

(65) Prior Publication Data

US 2020/0163724 A1    May 28, 2020

(51) Int. Cl.
| | |
|---|---|
| G08B 21/18 | (2006.01) |
| G06T 7/70 | (2017.01) |
| A61B 34/20 | (2016.01) |
| H05B 47/105 | (2020.01) |

(52) U.S. Cl.
CPC ............ A61B 34/20 (2016.02); G06T 7/70 (2017.01); G08B 21/18 (2013.01); H05B 47/105 (2020.01); *A61B 2034/2055* (2016.02); *A61B 2034/2065* (2016.02); *G06T 2207/30041* (2013.01); *G06T 2207/30052* (2013.01)

(58) Field of Classification Search
CPC .................................. G02B 1/12; A61B 3/107
See application file for complete search history.

(56) References Cited

U.S. PATENT DOCUMENTS

| | | | |
|---|---|---|---|
| 4,993,790 A | 2/1991 | Vick | |
| 6,563,565 B2 | 5/2003 | Nishi | |
| 6,905,641 B2 | 6/2005 | Platt et al. | |
| 7,105,110 B2 | 9/2006 | Platt et al. | |
| 7,377,643 B1 | 5/2008 | Chock et al. | |
| 8,177,778 B2 | 5/2012 | Muller et al. | |
| 8,202,272 B2 | 6/2012 | Muller et al. | |
| 8,348,935 B2 | 1/2013 | Muller et al. | |
| 8,366,689 B2 | 2/2013 | Marshall et al. | |
| 8,398,628 B2 | 3/2013 | Muller | |
| 8,409,189 B2 | 4/2013 | Muller | |
| 8,459,794 B2 | 6/2013 | Juhasz et al. | |

(Continued)

FOREIGN PATENT DOCUMENTS

WO    WO 2002/26121 A1    4/2002

*Primary Examiner* — Joshua L Schwartz

(57) ABSTRACT

A Light Adjustable Lens (LAL) Tracker comprises an Imaging System, for creating a LAL image by imaging a LAL implanted into an eye; and an Image Recognition System, coupled to the Imaging System, for determining a disk cross-correlator with the LAL image; determining an edge cross-correlator with the LAL image; and determining a LAL position by determining a combined cross-correlator from the disk cross-correlator and the edge cross-correlator. A Tracking-based Illumination Control System comprises the LAL Tracker for tracking a LAL implanted in an eye, including an Imaging System, and an Image Recognition System; and an Illumination Controller, coupled to the LAL Tracker, configured for determining a LAL misalignment factor, corresponding to a LAL misalignment that characterizes a misalignment of the LAL position with a LAL illumination pattern, and generating an illumination control signal in relation to the determined LAL misalignment factor.

23 Claims, 23 Drawing Sheets

(56) References Cited

U.S. PATENT DOCUMENTS

| | | |
|---|---|---|
| 8,460,278 B2 | 6/2013 | Muller |
| 8,469,952 B2 | 6/2013 | Muller et al. |
| 8,545,487 B2 | 10/2013 | Muller et al. |
| 8,574,277 B2 | 11/2013 | Muller et al. |
| 8,652,131 B2 | 2/2014 | Muller et al. |
| 8,662,667 B2 | 3/2014 | Schuhrke et al. |
| 8,712,536 B2 | 4/2014 | Muller et al. |
| 8,870,934 B2 | 10/2014 | Muller et al. |
| 8,882,757 B2 | 11/2014 | Muller et al. |
| 8,992,516 B2 | 3/2015 | Muller et al. |
| 9,020,580 B2 | 4/2015 | Friedman et al. |
| 9,044,308 B2 | 6/2015 | Muller et al. |
| 9,498,114 B2 | 11/2016 | Friedman et al. |
| 9,498,122 B2 | 11/2016 | Friedman et al. |
| 9,498,642 B2 | 11/2016 | Muller et al. |
| 9,707,126 B2 | 7/2017 | Friedman et al. |
| 9,950,482 B2 | 4/2018 | Grubbs et al. |
| 10,028,657 B2 | 7/2018 | Friedman |
| 2002/0100990 A1* | 8/2002 | Platt ................. A61F 2/1635 264/1.38 |
| 2005/0192563 A1 | 9/2005 | Platt et al. |
| 2010/0152847 A1* | 6/2010 | Padrick ................. A61B 3/13 623/6.11 |
| 2011/0019150 A1 | 1/2011 | Schuhrke et al. |
| 2013/0072591 A1* | 3/2013 | Sandstedt ............... B29C 35/00 522/148 |
| 2013/0245536 A1 | 9/2013 | Friedman et al. |
| 2014/0024997 A1 | 1/2014 | Muller et al. |
| 2014/0025049 A1 | 1/2014 | Muller et al. |
| 2014/0066835 A1 | 3/2014 | Muller et al. |
| 2014/0113009 A1 | 4/2014 | Muller et al. |
| 2014/0268040 A1 | 9/2014 | Mujat et al. |
| 2014/0276361 A1 | 9/2014 | Herekar et al. |
| 2014/0277431 A1 | 9/2014 | Herekar et al. |
| 2014/0320819 A1 | 10/2014 | Muller et al. |
| 2014/0340635 A1* | 11/2014 | Oyaizu ................ A61B 3/1005 351/206 |
| 2014/0343480 A1 | 11/2014 | Kamaev et al. |
| 2014/0368792 A1 | 12/2014 | Friedman et al. |
| 2014/0368793 A1 | 12/2014 | Friedman et al. |
| 2015/0025440 A1 | 1/2015 | Muller et al. |
| 2015/0100012 A1 | 4/2015 | Muller |
| 2015/0104087 A1 | 4/2015 | Katuwal et al. |
| 2015/0265762 A1 | 9/2015 | Friedman et al. |
| 2016/0139390 A1 | 5/2016 | Bukshtab et al. |
| 2016/0175442 A1 | 6/2016 | Kamaev et al. |
| 2016/0310319 A1 | 10/2016 | Friedman et al. |
| 2016/0310758 A1 | 10/2016 | Friedman et al. |
| 2016/0338588 A1 | 11/2016 | Friedman |
| 2016/0339657 A1* | 11/2016 | Grubbs ................ A61F 2/1627 |
| 2017/0021021 A1 | 1/2017 | Kamaev et al. |
| 2017/0156926 A1 | 6/2017 | Friedman et al. |
| 2017/0296383 A1 | 10/2017 | Friedman et al. |
| 2018/0206719 A1 | 7/2018 | Adler et al. |
| 2018/0232048 A1 | 8/2018 | Popovich et al. |
| 2018/0235808 A1 | 8/2018 | Muller et al. |
| 2018/0236077 A1 | 8/2018 | Friedman et al. |
| 2019/0018235 A1 | 1/2019 | Ouderkirk et al. |
| 2019/0041634 A1 | 2/2019 | Popovich et al. |

\* cited by examiner

TRACKING-BASED ILLUMINATION CONTROL SYSTEM

TECHNICAL FIELD

This invention relates to imaging and illuminating light adjustable lenses, and more specifically to systems and methods to control the illumination based on the imaging and tracking of the light adjustable lens.

BACKGROUND

The techniques of cataract surgery are experiencing continuous, impressive progress. Generations of phacoemulsification platforms and more recently introduced surgical lasers keep increasing the precision of the placement of intraocular lenses (IOLs) and keep reducing unwanted medical outcomes. Nevertheless, after the IOLs have been implanted, the postsurgical healing process shifts and rotates the IOLs in a non-negligible fraction of the patients, leading to a diminished visual acuity. A new technique has been developed recently to correct or mitigate this postsurgical IOL shift. The underlying idea is to adjust the IOLs postsurgically by applying a suitable illumination. As described, e.g. in commonly owned U.S. Pat. No. 6,905,641, to Platt et al, entitled: "Delivery system for post-operative power adjustment of adjustable lens", hereby incorporated by reference in its entirety, the IOLs can be fabricated from a photo-adjustable material, henceforth making them Light Adjustable Lenses, or LALs. After the implanted LALs settled and shifted post-surgically, the LALs can be illuminated by an irradiation system with an illumination pattern that induces a change in the shape and possibly in the index of refraction of the LALs, such that their optical power is modified. The illumination pattern can be chosen such that the induced optical power change compensates the unintended post-surgical shift of the LAL.

An important aspect of this process is the need to align the illumination pattern and the LAL, to ensure that the illumination pattern causes the intended power change. The power change caused by a misaligned illumination pattern may not compensate the post-surgical LAL shift effectively. Such misalignment can be caused by the patient's eye movements, such as saccadic eye motion, breathing, and involuntary movements by either the patient or the physician.

In some illumination procedures, the misalignment between the eye and the illumination by the Light Delivery System, or LDD, can be compensated by the physician manually in real time. The physician can look through the oculars of a biomicroscope of the LDD and maintain an overlap of a presented reticle and the image of the LAL by continuously applying small changes to either the position of the eye, or to the illumination pattern the LDD, or to both.

Problems of such approaches include that illumination procedures can require several minutes and maintaining the alignment through an entire duration of such a procedure can be difficult and tiring for the physician. Also, maintaining the alignment is one more skill the physicians need to master, and a lack of mastery of this skill is one more way the procedure can result in inferior visual acuity. Therefore, there is a clear medical need to assist the physician to align the illumination pattern with the implanted LAL during the lens adjustment procedure. Automating any aspect of the LAL-illumination alignment can be valuable to reduce the demand on the physician, to reduce the skills required of the physician, and thus to improve the visual outcome of the adjustment procedure.

SUMMARY

The above-described medical needs can be addressed by the following embodiments. A Light Adjustable Lens (LAL) Tracker, comprising an Imaging System, for creating a LAL image by imaging a LAL implanted into an eye; and an Image Recognition System, coupled to the Imaging System, for determining a disk cross-correlator with the LAL image; determining an edge cross-correlator with the LAL image; and determining a LAL position by determining a combined cross-correlator from the disk cross-correlator and the edge cross-correlator.

In some embodiments, a method of tracking a Light Adjustable Lens (LAL) is comprising: creating a Light Adjustable Lens (LAL) image by imaging a LAL implanted into an eye with an Imaging System; determining a disk cross-correlator with an Image Recognition System; determining an edge cross-correlator with the Image Recognition System; and determining an LAL position by determining a combined cross-correlator from the disk cross-correlator and the edge cross-correlator, using the Image Recognition System.

In some embodiments, a Tracking-based Illumination Control System is comprising a Light Adjustable Lens (LAL) Tracker for tracking a LAL implanted in an eye, including an Imaging System, for creating a LAL image by imaging the LAL, and an Image Recognition System, coupled to the Imaging System, for determining a LAL position in a reference frame based on the LAL image; and an Illumination Controller, coupled to the LAL Tracker, configured for determining a LAL misalignment factor, corresponding to a LAL misalignment that characterizes a misalignment of the LAL position with a LAL illumination pattern, and generating an illumination control signal in relation to the determined LAL misalignment factor.

In some embodiments, a method of operation of a Tracking-based Illumination Control System, the method comprising the steps of tracking a Light Adjustable Lens (LAL), implanted in an eye, by a LAL Tracker, including creating a LAL image by imaging the LAL with an Imaging System, and determining a LAL position based on the LAL image by an Image Recognition System, coupled to the Imaging System; determining a LAL misalignment factor corresponding to a LAL misalignment that characterizes a misalignment of the LAL position with a LAL illumination pattern, by an Illumination Controller, coupled to the LAL Tracker; and generating an illumination control signal in relation to the determined LAL misalignment factor by the Illumination Controller.

DETAILED DESCRIPTION

Figure 1:
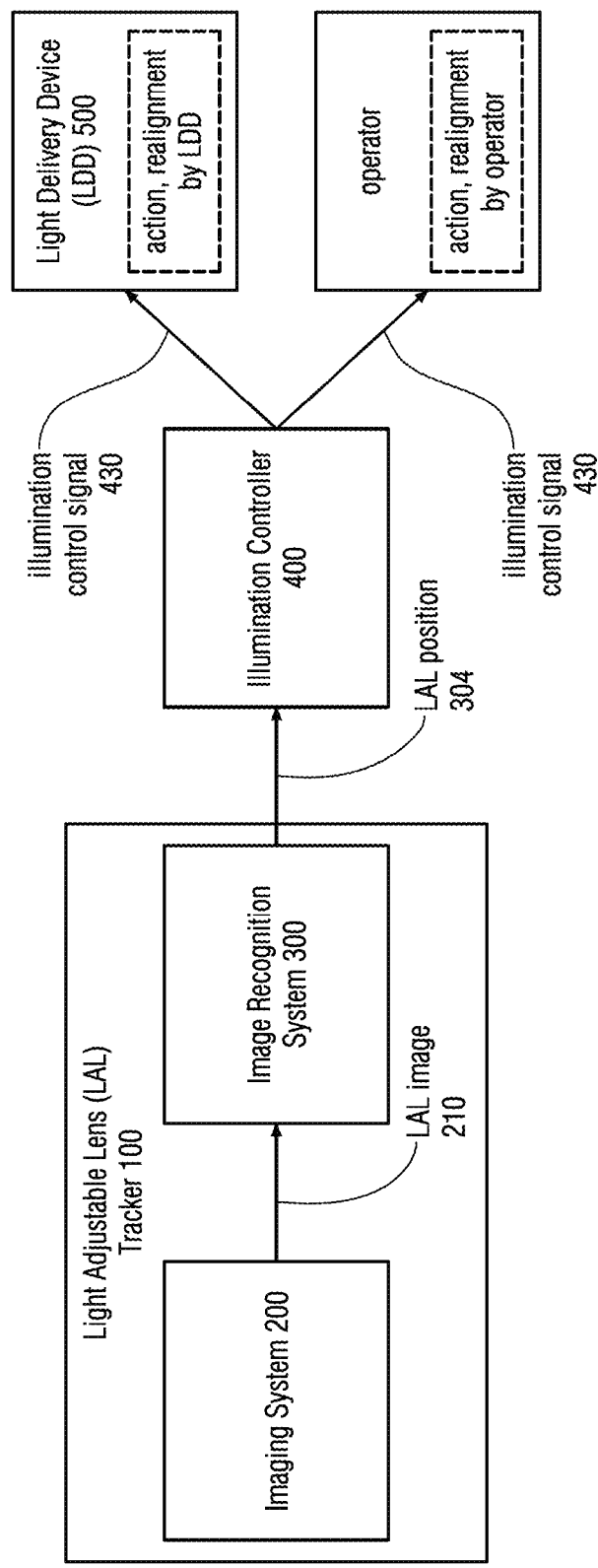
FIG. 1 illustrates a Tracking-based Illumination Control System.

This document describes a system that addresses the above described medical needs. The first part of the document describes embodiments of a Light Adjustable Tracking System and method, directed toward detecting and imaging an implanted Light Adjustable Lens (LAL), in order to determine its position and misalignment relative to a relevant reference frame. In the second part, a Tracking-based Illumination Control System is described that can either reduce the misalignment between the implanted LAL and an illumination system, based on the determined position of the LAL, or can control the illumination based on the misalignment.

A misalignment of the illumination system, in particular its Light Delivery Device (LDD) with the LAL is of high importance because a misaligned illumination can adjust the optical properties of the LAL in an unplanned manner, as well as lead to undesirable outcomes. Therefore, aligning the illumination with the LAL is of substantial medical benefit. The here-described system is configured to assist the operator of the illumination system to improve the alignment between the illumination system and the LAL. This assistance allows the operator, typically a physician, to improve and maintain the alignment with a higher precision. Operating the described systems therefore require less effort and skill, so that the physician can focus on the other aspects of the illumination process. All these aspects of the described systems and methods lead to medical outcomes with better visual acuity.

Light Adjustable Lens Tracking System and Method

FIGS. 1-9 illustrate a Light Adjustable Lens (LAL) Tracker 100, comprising an Imaging System 200, for creating a LAL image 210 by imaging a LAL 10 implanted into an eye; and an Image Recognition System 300, coupled to the Imaging System 200, for determining a disk cross-correlator 301 with the LAL image 210; determining an edge cross-correlator 302 with the LAL image 210; and determining a LAL position 304 by determining a combined cross-correlator 303 from the disk cross-correlator 301 and the edge cross-correlator 302. The LAL Tracker 100 can output the LAL position 304 toward an Illumination Controller 400, which in turn can generate an illumination control signal 430. This illumination control signal 430 can prompt either an operator, or a Light Delivery Device (LDD) 500 for either a responsive action, or a realignment, as described in detail later.

In some embodiments, the Imaging System 200 images the LAL 10 using an infrared wavelength imaging light. During the illumination procedure, various light sources can be present. Besides the ambient light sources, often eye-fixation lights, or Light Emitting Diodes (LEDs), and 4-8 illumination LEDs are employed to make the eye well-lit for the physician. All these light sources reflect not only from the cornea, but from the inner layers of the eye, causing so-called Purkinje reflections. These numerous Purkinje reflections can be quite disorienting and confusing from an imaging point of view. Since most of these illumination and fixation lights operate only in the visible range and have no infrared component, some embodiments of the Imaging System 200 prevent imaging confusion by using infrared light for the imaging.

Since the Imaging System 200 is providing real-time image of the eye, in some embodiments video imaging systems can be employed. The inherent noise of the imaging process can be reduced by creating an image via averaging a few video frames, such as averaging 2-10 frames. The frame rate of these video imaging systems can be suitably chosen: it can be below 20 frame/sec, about 20 frames/sec, or above 20 frames/sec.

Figure 2:
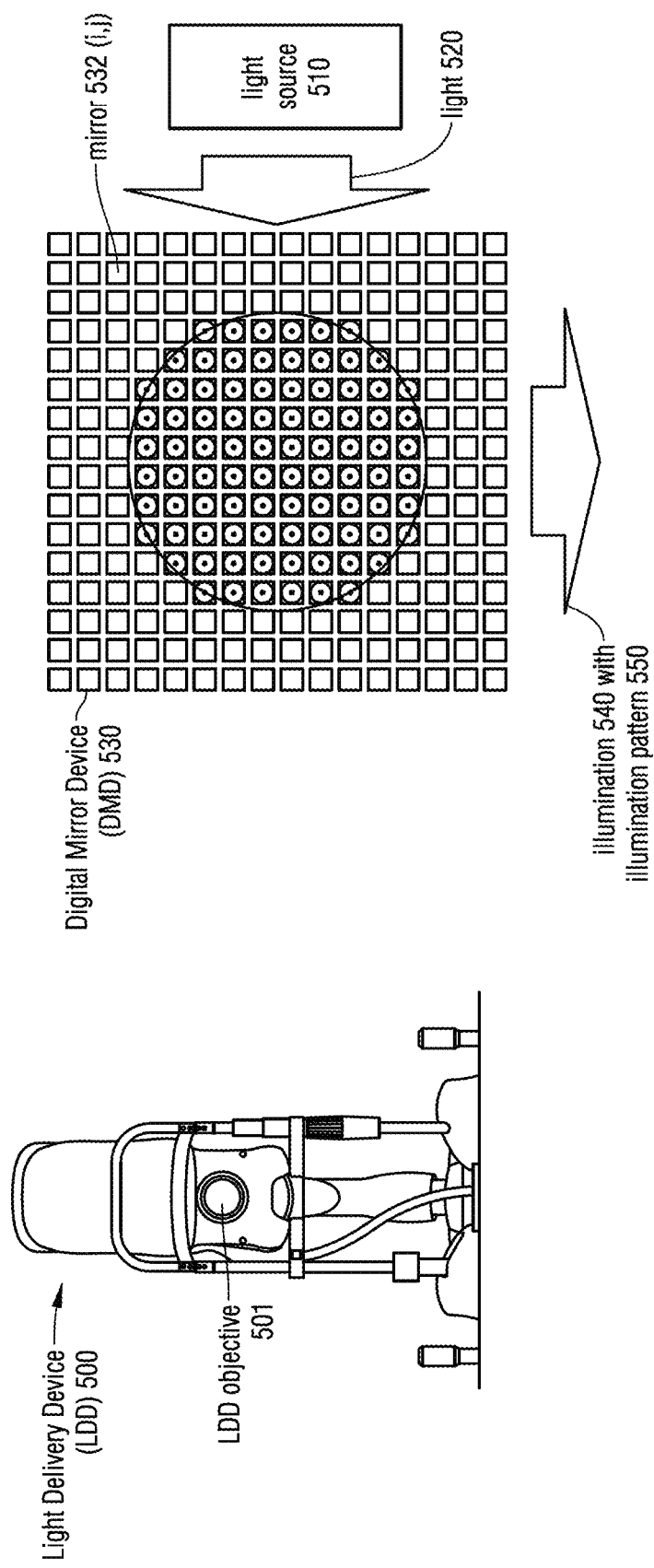
FIG. 2 illustrates a Light Delivery Device (LDD).

FIG. 2 illustrates an embodiment of the Light Delivery Device (LDD) 500. The left panel shows a patient-facing image of the LDD 500. The illumination is applied through the LDD objective 501. The LAL Tracker 100 can be implemented fully or partially integrated with the LDD 500. For example, an optical portion, or an imaging portion of the LAL Tracker 100, or both can be co-housed with the optics of the LDD 500, while a computer portion of the LAL Tracker 100 can be housed separately.

The right panel shows that, in some embodiments, the LDD 500 can include a light source 510, that can be a UV light source, a mercury arc-light, an LED, an LED array, a laser, a scanned light source, a pulsed light source, or a continuous-wave light source. The light source 510 can generate a light 520 that is directed to a patterning system. In some embodiments, this patterning system can be a Digital Mirror Device (DMD) 530. The DMD 530 can include a large array of micro-mirrors 532(i,j) that can be individually controlled. In a standard DMD arrangement, the mirrors 532(i,j) can be switched between an on and an off position. The on-mirrors 532 deflect the incoming light 520, the off-mirrors 532 let the light 520 pass by. Many other embodiments of a patterning system are also possible, including transmission-controlled embodiments, LCD-based embodiments, deformable mirrors, and actuated mirrors. All these embodiments can deflect, or redirect, the generated light 520 as an illumination 540 with an illumination pattern 550.

Figure 3:
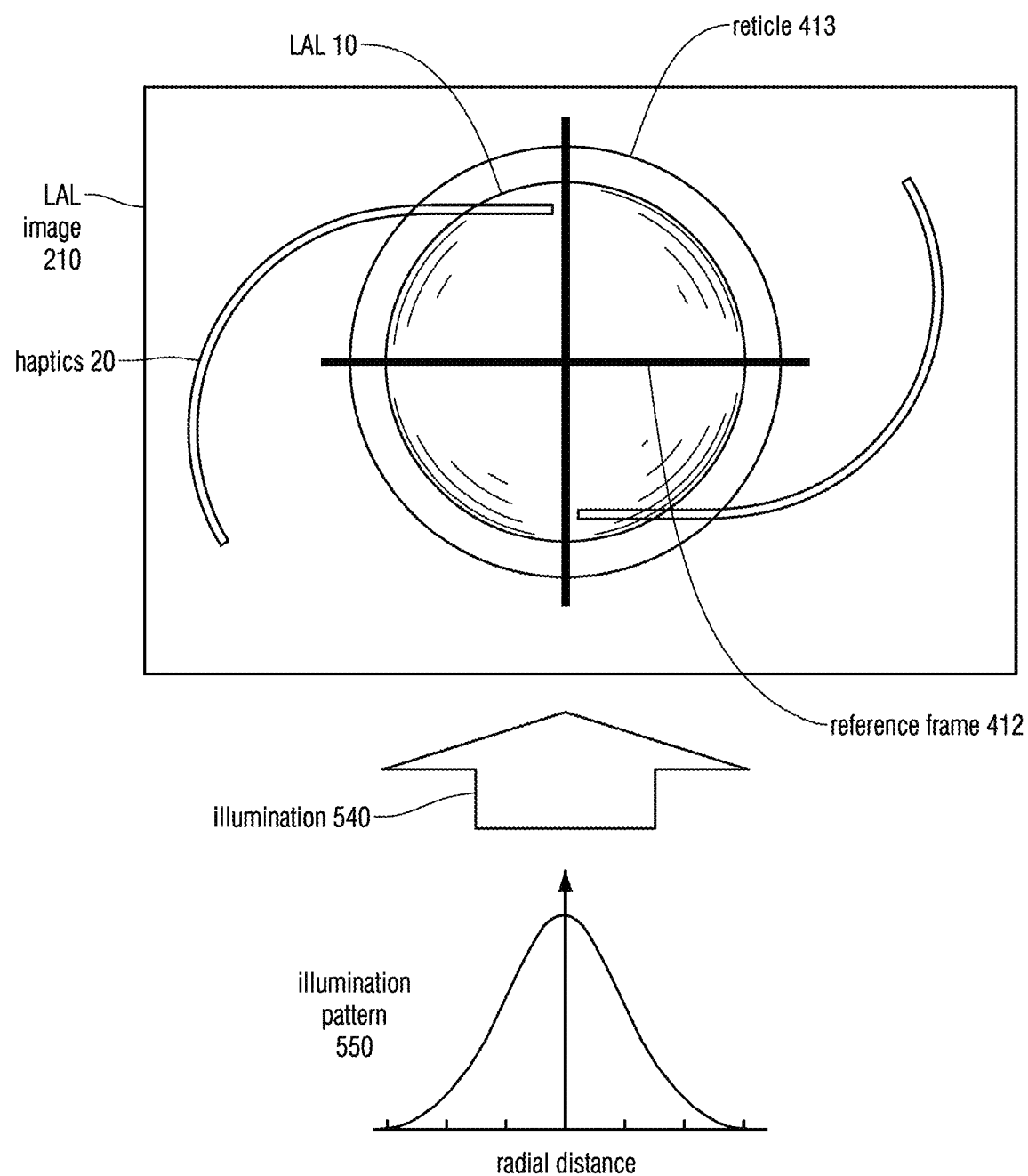
FIG. 3 illustrates an illumination alignment.

FIG. 3 illustrates the alignment of the LAL 10 with the illumination 540 with the illumination pattern 550. The illumination pattern 550 is shown as a Gaussian-like pattern, typically centered in the reference frame 412 as a function of a radial distance from an optical axis. Haptics 20 of the LAL 10 are also shown. The optical axis can be the optical axis of the LDD 500. In some embodiments, the illumination pattern 550 may be adjustable. These embodiments may allow the shifting of the illumination pattern 550 off the optical axis of the LDD 500.

The Imaging System 200 can create the LAL image 210. This can be in an ocular of a biomicroscope of the LDD 500. Other embodiments can employ a separate video microscope, or video display. Aligning the illumination 540 and its illumination pattern 550 with the LAL 10 can be assisted by a reference frame 412, as e.g. provided via a presented, or apparent, reticle 413.

Many embodiments are possible here. The reference frame 412, sometimes called the reference system 412, can be a reference system of, or referenced to, the Imaging System 200, the Image Recognition System 300, the Illumination Controller 400, or the LDD 500. Some, or all of these systems 200-500 can share some or all of their optical pathway, and thus may share their reference system 412. The reference frame/system 412 can be presented for the operator, typically a physician, in a convenient manner via the reticle 413. The reticle 413 can be a circle, centered at the origin of the reference frame 412. The circle can be continuous or segmented. It can be a set of concentric circles. The reticle 413 can also be a crosshair, a square, or a combination of the previously described embodiments. The reticle 413, and thus the reference frame 412, can be coupled into the optical system of the Light Delivery Device 500, e.g., via a beam splitter and a mirror that reflects differently in the visible and the IR. In other embodiments, the reticle 413, and thus the reference frame 412, can also be electronically generated in the LAL Tracker 100, or the Illumination Controller 400. In all of these embodiments, the reticle 413, and thus the reference frame 412, can be indicative of a center of the illumination pattern 550 of the LDD 500. As described before, embodiments with different choices of the reference frame 412 and reticle 413 can all be useful for determining the misalignment of the LAL position 304 relative to the illumination pattern 550.

In these embodiments, one of the tasks is to align the LAL 10 with the reference frame 412. As mentioned before, this can be achieved by adjusting or shifting either the illumination pattern 550, or the eye, or both. In some typical embodiments, the center of the LAL 10 can be aligned with the center of the reference frame 412. In other embodiments, the perimeter of the LAL 10 can be aligned with the reticle 413. Many analogous alignment techniques can be implemented as well.

The LAL alignment can be achieved by the physician manually moving or rotating the eye, while watching the LAL position 304 on the LAL image 210. In some embodiments, the physician can place a contact lens on the eye and rotate the eye by manually manipulating the contact lens.

The LAL Tracker 100 can be set up to assist, and to partially automate this alignment process by utilizing the Image Recognition System 300. This Image Recognition System 300 can be formed for determining the LAL position 304 relative to the reference system 412. In some typical embodiments, the LAL position 304 refers to the position of the center of the LAL 10. Once the Image Recognition System 300 determined the LAL position 304, the operator can improve the alignment of the illumination pattern 550 with the LAL 10 by adjusting the eye, the LDD, or both, to align the center of the illumination pattern 550 with the determined LAL (center) position 304.

In other embodiments, the Image Recognition System 300 can electronically and directly prompt the illumination of the LDD 500 with the illumination control signal 430 for a responsive action once a misalignment has been detected, as described below.

The described techniques and systems can minimize and manage the LAL-LDD misalignment accurately if the LAL position 304 is determined accurately. FIGS. 4-7 describe in detail how the LAL Tracker 100 can determine the LAL position 304 accurately.

Figure 4A:
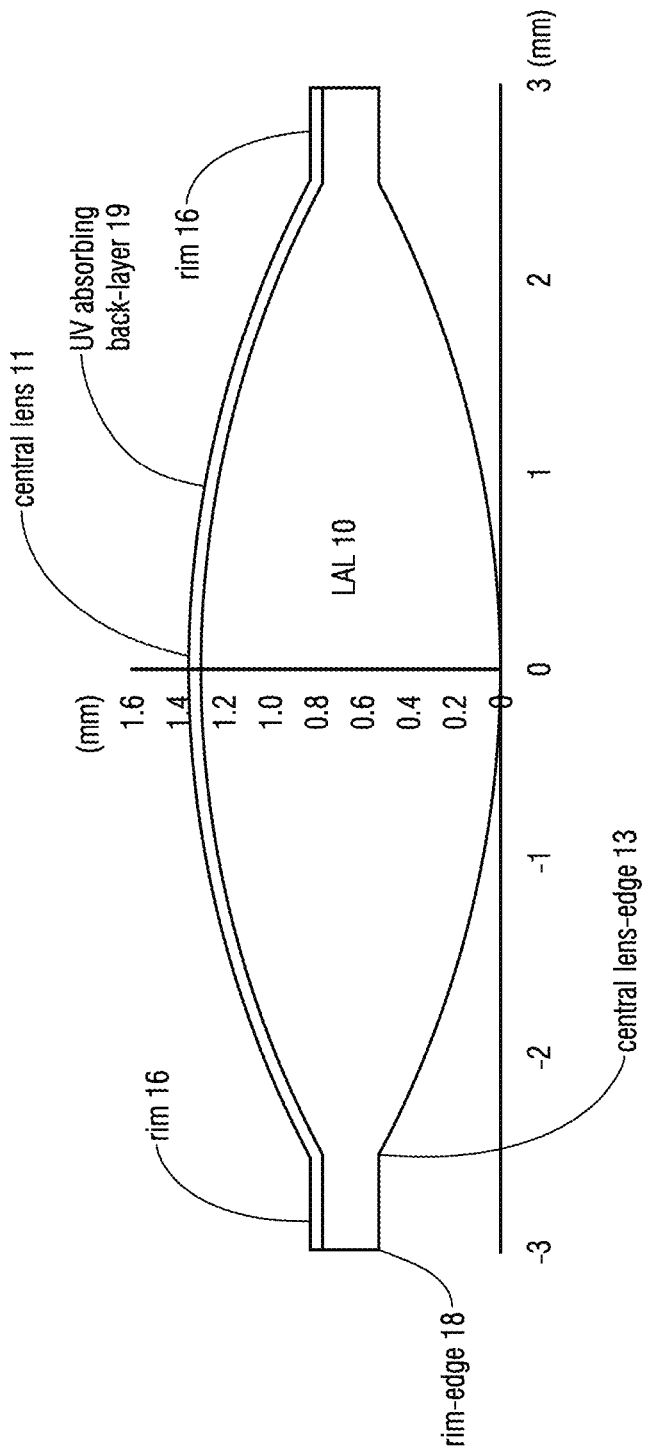
FIGS. 4A-B illustrate a Light Adjustable Lens (LAL), and its image.
Figure 4B:
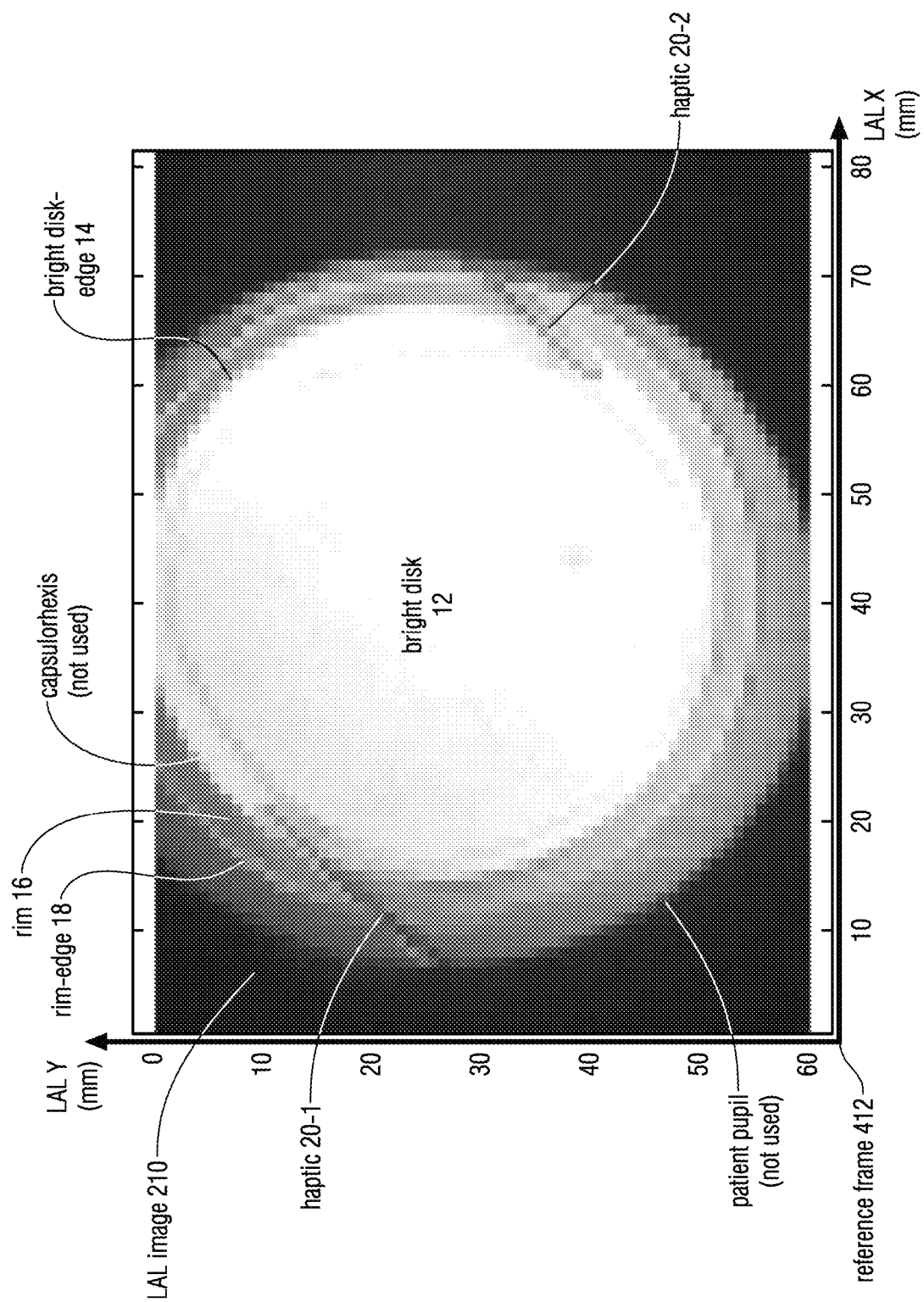

FIGS. 4A-B illustrate the context of this imaging challenge. FIG. 4A shows that typical embodiments of the LAL 10 include a central lens 11, which has a curvature on both sides, and accordingly has an optical refractive power. Typical values of this refractive power are in the 10-30 diopter (D) range. A majority of the LALs have optical powers within a few diopter range around 20 D. The central lens 11 has a strong optical power and thus focuses light very effectively, and therefore it typically shows up as a bright disk 12 in the LAL image 210, as shown in FIG. 4B.

The central lens 11 is surrounded by a central lens-edge 13, which shows up as a bright-disk edge 14 in the LAL image 210. This central lens-edge 13 can be surrounded by a rim 16, which typically has no associated optical power, and therefore it is distinctly less bright than the bright disk 12 in the LAL image 210. The rim 16 is bounded by a rim-edge 18. In relevant embodiments, the LAL 10 can also include a UV absorbing back-layer 19.

FIG. 4B shows that the LAL image 210 typically also captures an image of the haptics 20-1 and 20-2. The haptics 20-1/20-2 are most often implemented as a pair. The LAL image 210 is shown as pixillated in its most typical implementation, as a video image frame of a video imaging system that can involve a CCD camera. In this implementation, the Image Recognition System 300 is configured to determine the LAL position 304 as a pixel position in the reference frame 412, that can be referenced, or translated into the pixel positions of the video imaging system.

Figure 5A:
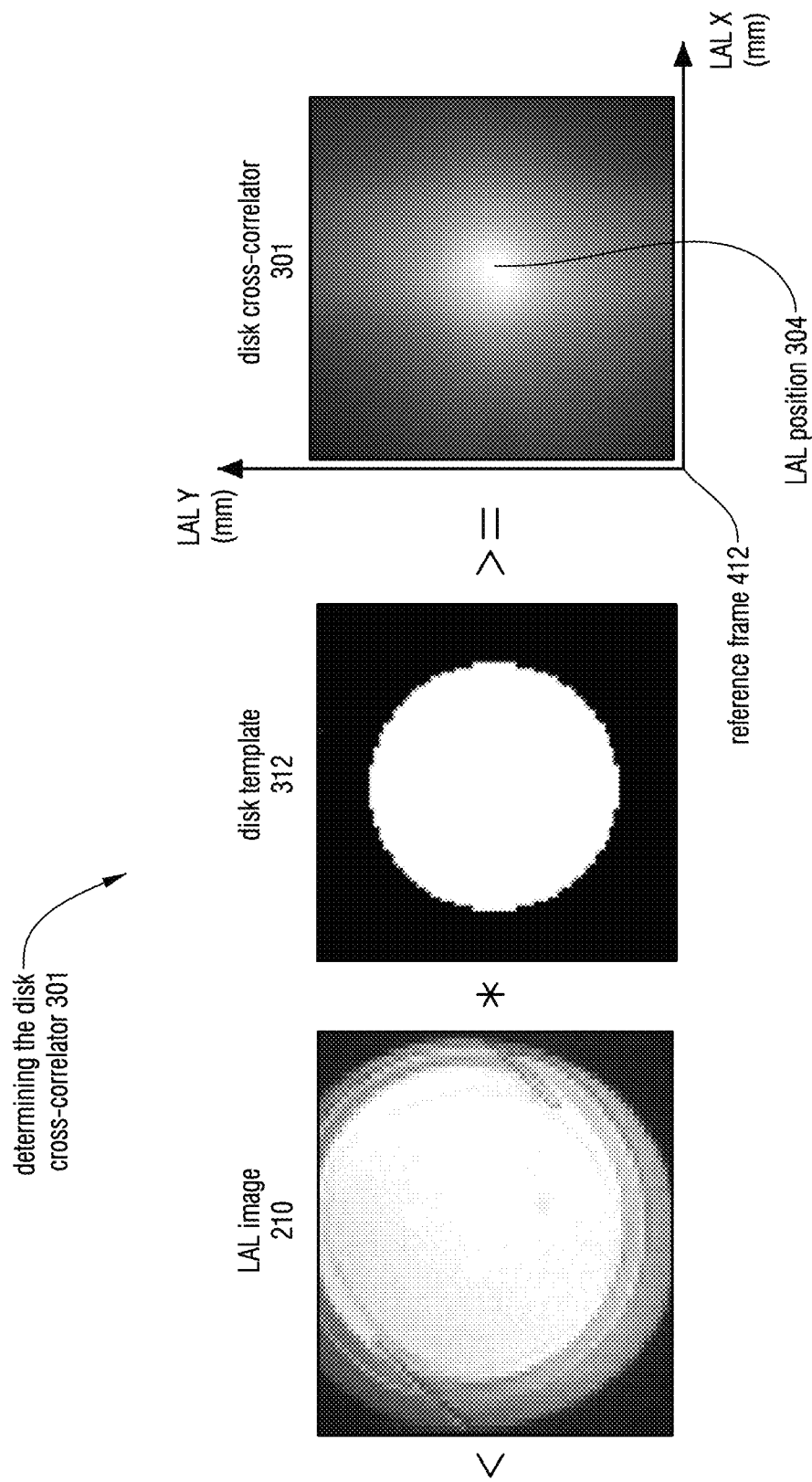
FIGS. 5A-B illustrate determining a disk cross-correlator.
Figure 5B:
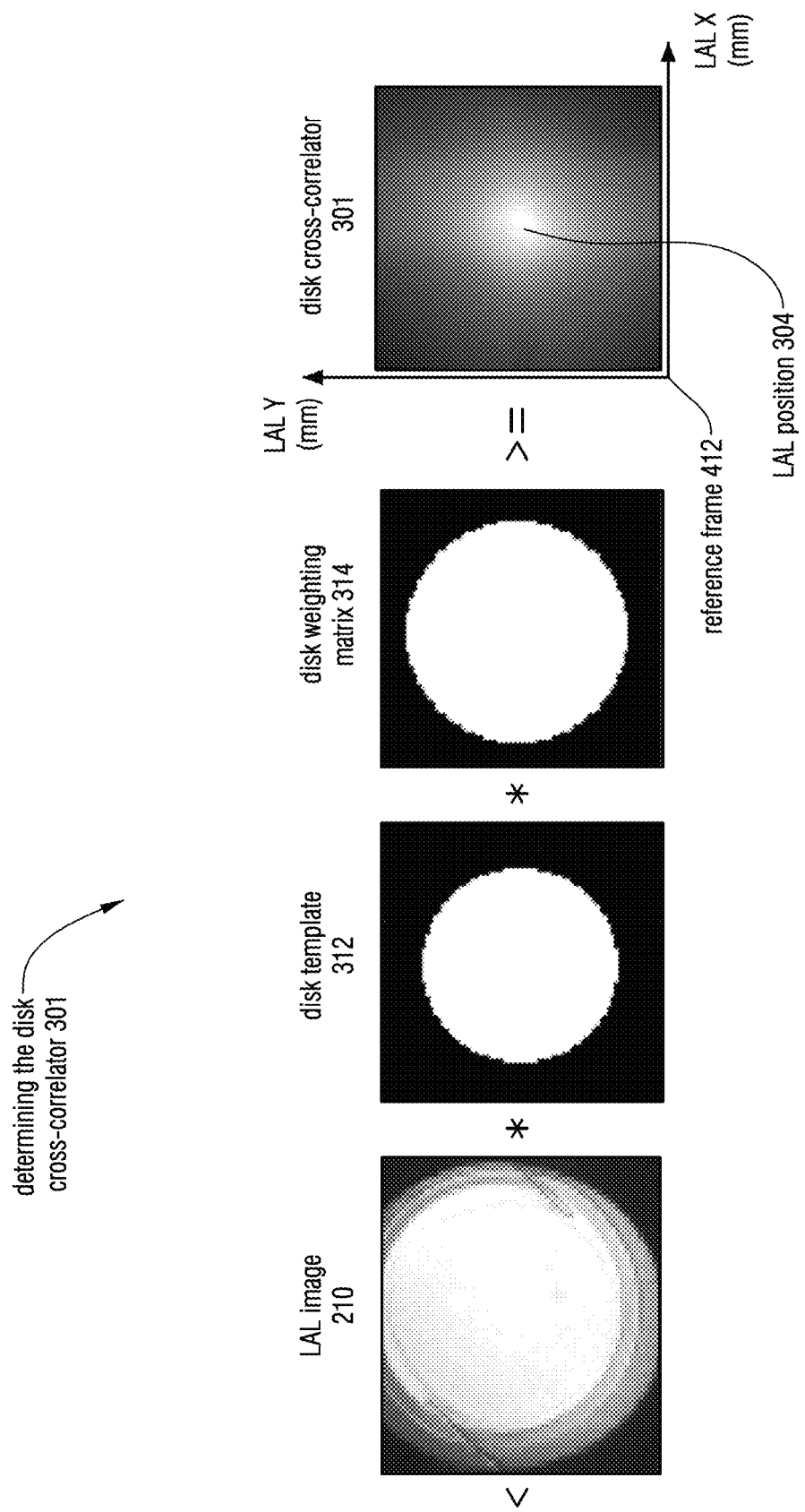
Figure 6A:
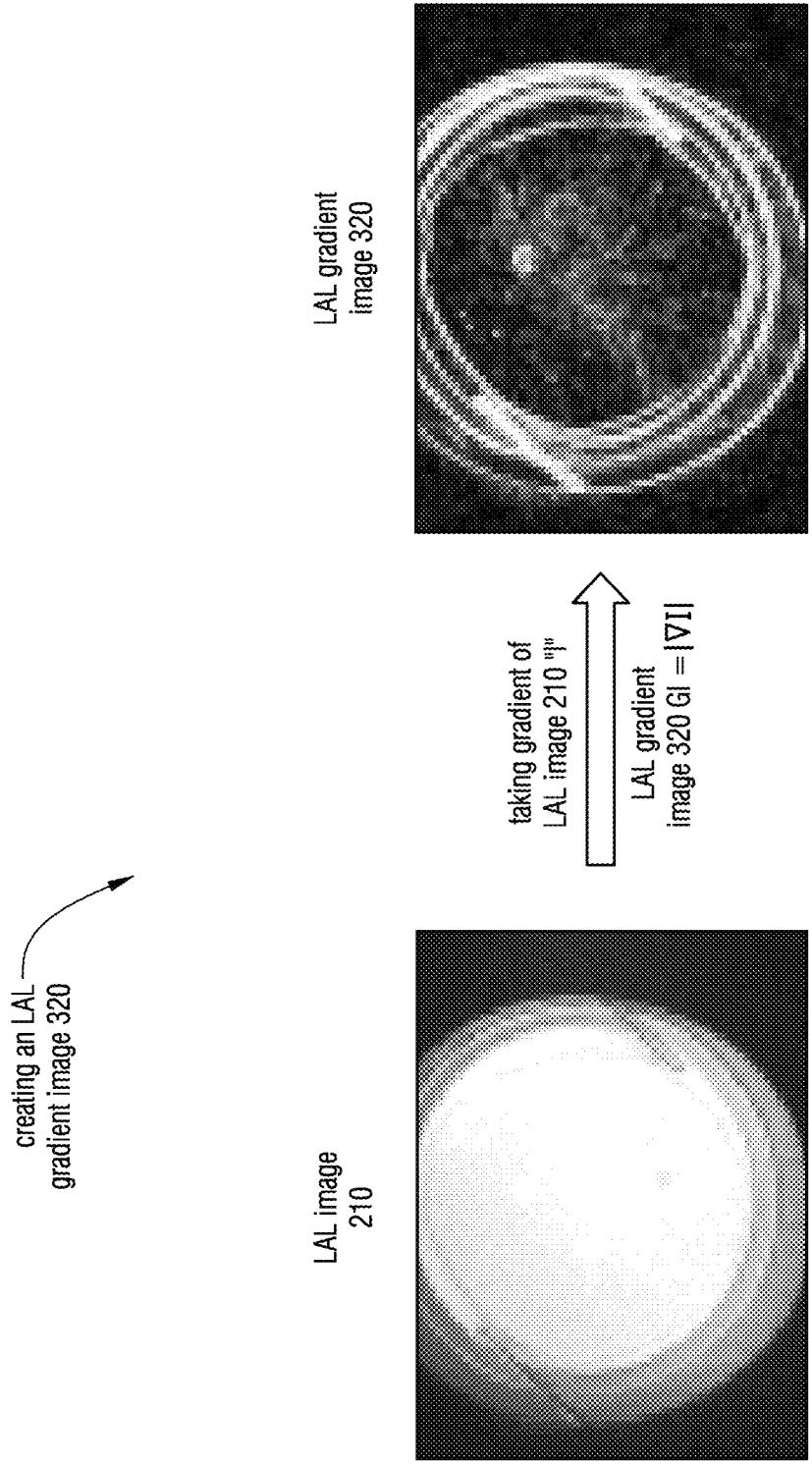
FIGS. 6A-C illustrate determining an edge cross-correlator.
Figure 6B:
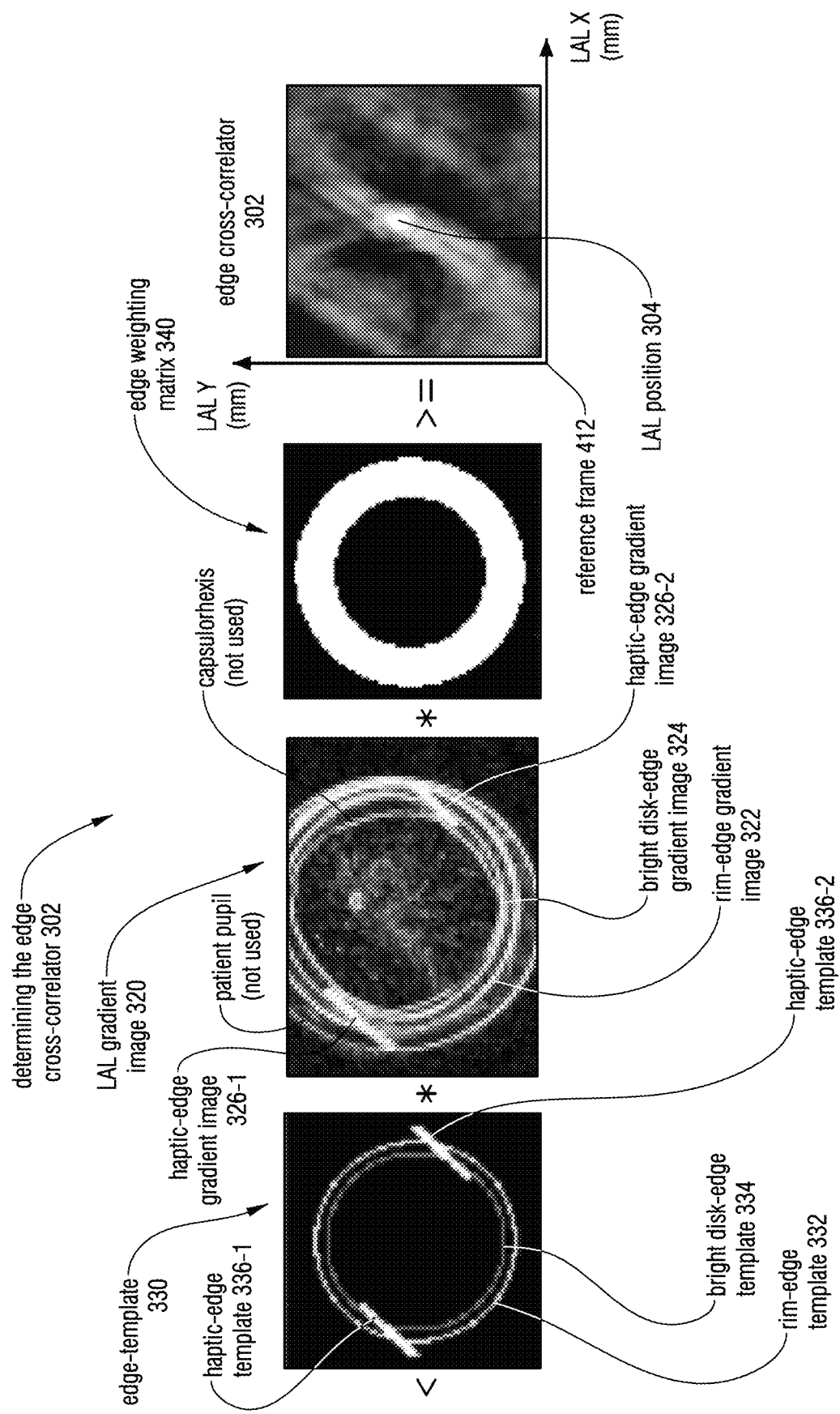
Figure 6C:
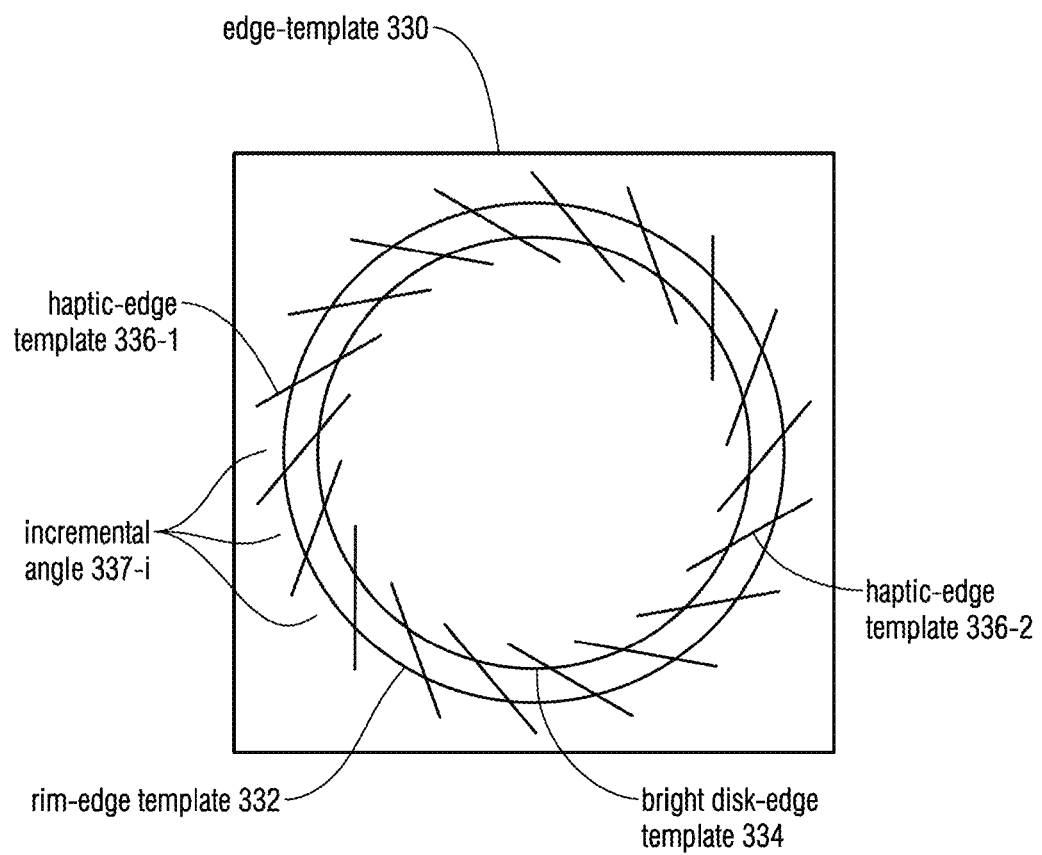
Figure 7:
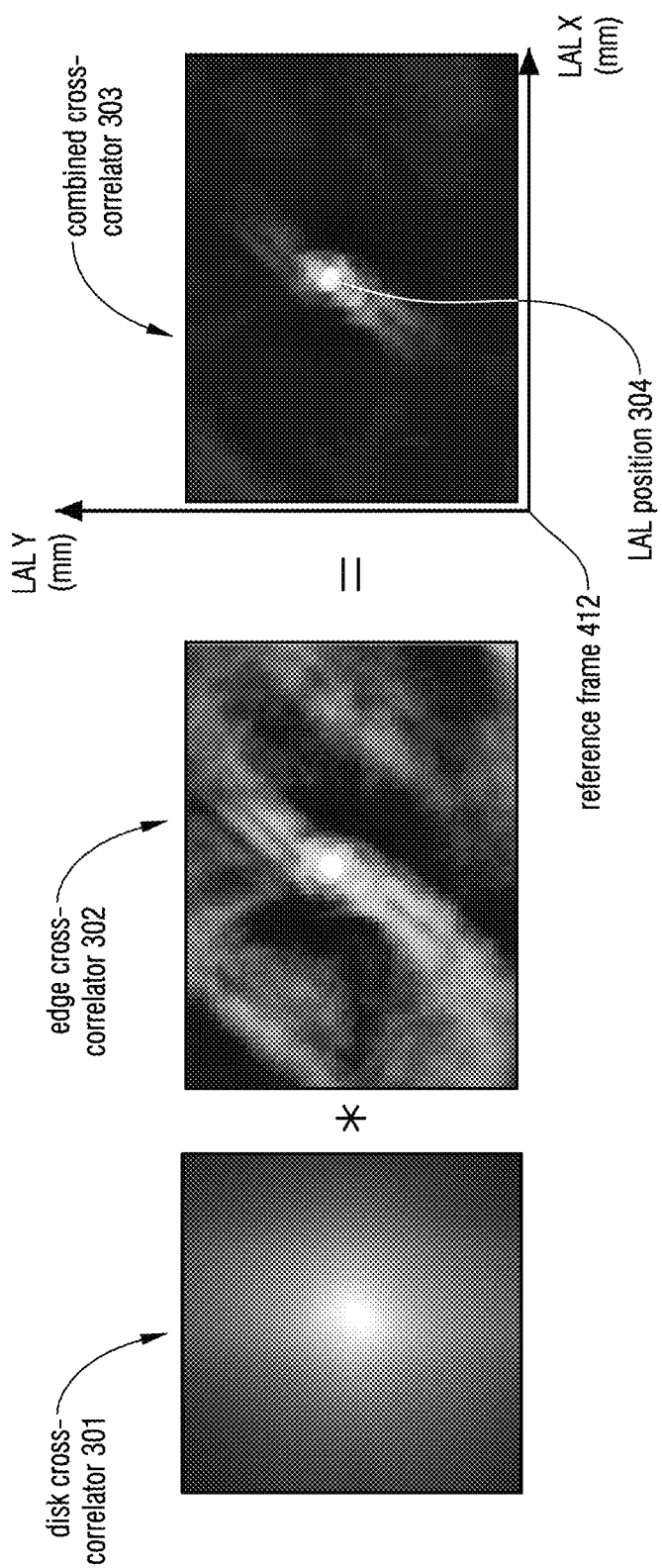
FIG. 7 illustrates determining a combined cross-correlator.

FIGS. 5-7 illustrate in detail the process of determining the LAL positions 304. FIG. 5A illustrates that the Image Recognition System 300 can be configured for determining the disk cross-correlator 301 as a cross-correlation function between a disk-template 312 and the LAL image 210, wherein the disk-template 312 is an expected image of the bright disk 12, generated by the central lens 11 of the LAT. 10. Since the specifics of the optical system of the Imaging System 200 and the LAL 10 are known, the disk-template 312 as the expected image of the LAL 10 can be constructed quite accurately. FIG. 5B illustrates that in some embodiments the cross-correlation function includes a disk weighting matrix 314. The above-mentioned cross-correlators and cross-correlation functions can be normalized. In equations, the above can be expressed as:

$$C_{m,n} = \frac{\sum_{i,j} I'_{m+i,n+j} T'_{i,j} W_{i,j}}{\sqrt{\sum_{i,j} (I'_{m+i,n+j} W_{i,j})^2 \sum_{i,j} (T'_{i,j} W_{i,j})^2}} \quad (1)$$

wherein:

$$I'_{i,j} = I_{i,j} - \langle W_{i,j} I_{i,j} \rangle \quad T'_{i,j} = T_{i,j} - \langle W_{i,j} T_{i,j} \rangle \quad (2)$$

In Eq. (1), $I_{m+i,n+j}$ represents the value of the LAL image 210 in the (m+i,n+j) pixel, $T_{i,j}$ represents the value of the disk template 312 in the (i,j) pixel, and $W_{i,j}$ represents the value of the weighting matrix 314 in the (i,j) pixel. The pixel-by-pixel sum of the product convolution of the I, T and W matrices defines the cross-correlation function $C_{m,n}$. The square roots in the denominator are the normalization factors for the I and T matrices. In Eq. (2), the W-weighted averages of the I and T matrices have been factored out to define the I' and T' matrices. In FIGS. SA-B, the <A*B> and <A*B*C> notations represent convolving the A and B, and the A, B, and C matrices on an element-by-element basis, and then summing up their products, as e.g. indicated in Eq. (1).

The LAL image 210 $I_{m+i,n+j}$ is expected to take the shape of, or fit, the disk template 312 $T_{i,j}$. An unknown of this fitting is the LAL position 304 in the reference frame 412. In some embodiments, the disk template 312 $T_{i,j}$ is centered with the reference frame 412. The LAL position 304 can be determined by assuming that the LAL image 210 I is shifted relative to the disk-template 312 T by a shift vector (m,n), and then determining the normalized cross-correlator $C_{m,n}$ by scanning across the space of all reasonable values of this shift-vector (m,n). $C_{m,n}$ expresses how well the shifted image $I_{m+i,n+j}$ is represented by the centered disk template 312 $T_{i,j}$. The cross correlation function $C_{m,n}$ is expected to show a maximum when the shift vector (m,n) coincides with the LAL (center) position 304. Of course, in analogous embodiments, the LAL image 210 I can be kept centered, and the shift of the disk-template 312 T can be scanned. In yet other embodiments, both the LAL image 210 I and the disk template 312 T can be scanned. The shared aspect of these approaches is that the center of the LAL image 210 I and the center of the disk template 312 T are scanned relative to each other.

This scanning can be a straightforward raster scan across the entire (reasonable) position space. In other embodiments, it can be a directed, searching scan, using some variant of a search process, such as a gradient descent search, or a conjugate gradient method. Many other search methods are known in the art and can be used.

In some embodiments, optionally a disk weighting matrix 314 $W_{i,j}$ can be included to improve the efficiency and can reduce the noise of this procedure by eliminating, or de-weighting, those regions from the procedure that are well-separated from the bright-disk edge 14 and the rim-edge 18, and thus are not expected to contribute meaningfully to this image recognition process. For example, the disk-weighting matrix 314 $W_{i,j}$ can be a disk or a ring with some width around the expected bright disk-edge 14.

Several other embodiments of the disk cross-correlator 301, edge cross-correlator 302, and combined cross-correlator 303 can be used as well. In some technical descriptions, the weighting is referred to as masking, and thus, the weighting matrix 314 $W_{i,j}$ can also refer to a masking matrix 314 $W_{i,j}$. Further, a wide class of the here-described image recognition processes is often referred to as "template matching". Several template matching techniques are described on the website "Open Source Computer Vision", seven pages of which were captured at the time of filing this patent document, submitted herewith and incorporated in its entirety. Embodiments of such image recognition methods by template matching include CV_TM_SQDIFF; CV_TM_SQDIFF_NORMED; CV_TM_CCORR: CV_TM_CCORR_NORMED; CV_TM_CCOEFF; and CV_TM_CCOEFF_NORMED. Each of this template matching techniques can be practiced by the Image Recognition System 300. Another class of embodiments of the cross-correlators 301-303 can involve Hough transforms, of the line, circle or ellipse-based variety, or generalized Hough transforms. These Hough transforms can involve transforming the raw image data from a continuous, or analog grey scale to a single bit per pixel representation. In some cases it can involve a voting procedure in a parameter space.

FIG. 5B shows the disk cross-correlator 301 $C_{m,n}$ that emerges from the just-described procedure. The disk cross-correlator 301 $C_{m,n}$ clearly exhibits a maximum, that is the most likely LAL position 304. While this disk cross-correlator 301 has a clear maximum, the correlation function around the maximum is relatively smooth, and therefore, the LAL position 304 is not defined very sharply by the procedure based on the disk template 312 alone. Therefore, employing improvements that sharpen this maximum can enhance the efficiency of the determination of the LAL position 304.

FIGS. 6A-B show such an improvement. The Image Recognition System 300 can be further configured for creating a LAL gradient image 320 by determining a gradient of the LAL image 210:

$$G = |\nabla I| \qquad (3)$$

Here, I continues to denote the value of the LAL image 210. The LAL gradient image 320, denoted by G, is determined as the magnitude of the gradient vector of the image I. Taking the gradient captures the spatial change of the LAL image 210 very efficiently, as seen from the sharpness of the white contours, or lines, in the right panel of FIG. 6A.

FIG. 6B illustrates that the rest of the method of determining the edge cross-correlator 302 can be implemented analogously to the method of determining the disk cross-correlator 301, wherein the gradient image G takes the role of the image I. An edge-template 330 $T_{i,j}$ can be defined that includes the most relevant expected aspects of the LAL gradient image 320: a well-defined rim-edge template 332, and a bright disk-edge template 334, corresponding to the bright disk-edge 14, generated by the central lens-edge 13 of the LAL 10, and a haptic-edge template 336, corresponding to at least one haptic 20 of the LAL 10. For a more streamlined nomenclature, the contours that correspond to the haptics 20 in the LAL gradient image 320 and in the edge-template 330, are also referred to as a haptic-edge gradient image 326 and a haptic-edge template 336. The haptic-edge gradient images 326, and the haptic-edge templates 336 of the two haptics 20-1 and 20-2 are correspondingly labeled as -1 and -2. The edge cross-correlator 302 is determined as the cross-correlation function formed from the edge-template 330 $T_{i,j}$ and the LAL gradient image 320 $G_{m+i,n+j}$.

It is noted that, as seen in the LAL gradient image 320 in FIG. 4B, and in the second panels of FIG. 6A and FIG. 6B, the LAL gradient image 320 also includes an approximately circular image of the capsulorhexis, as well as the circular image of the aperture of the optics. In some of the here-described methods, these two, roughly circular images are not used, or referenced.

Finally, similarly to the technique described in FIGS. 5A-B, the cross-correlation function can optionally include an edge weighting matrix 340 W, to reduce the noise from the less-relevant portions of the LAL gradient image 320. The correlation function of these three functions, the LAL gradient image 320, the edge-template 330, and optionally the edge weighting matrix 340 yields the edge cross-correlator 302, as shown in FIG. 6B.

FIG. 6C illustrates a technical aspect of calculating the edge cross-correlator 302. While the edge-template 330 is built on the existing knowledge that the LAL gradient image 320 is expected to show the image of two haptics 20-1/2, the orientation of these two haptics 20-1/2 is not known. One way to handle this uncertainty is not to use a single haptic-edge template 336, as its orientation will typically not line up with the orientation of the actual haptics 20-1/2. Instead, to construct the correlation function of the LAL gradient image 320 with a haptic-edge template 336 oriented into a specific direction, and in the likely case of the correlation function indicating limited correlations, repeatedly rotating the haptic-edge template 336 by an incremental angle 337-i and re-calculating the correlation function until the best correlation is achieved. This incremental angle can be a few degrees in the 0-5 degrees range, in some embodiments, the incremental angle 337-i can be about 2 degrees.

FIG. 6B illustrates that the edge cross-correlator 302 also exhibits a peak in the reference frame 412, as did the disk cross-correlator 301, but this peak is much sharper, and thus predicts the LAL position 304 with higher confidence.

FIG. 7 illustrates the next step of the procedure: generating the combined cross-correlator 303 as product of the disk cross-correlator 301 and the edge-cross-correlator 302. Visibly, this combined cross-correlator 303 exhibits an even sharper peak than either the disk cross-correlator 301, or the edge cross-correlator 302, thus enabling the determination of the LAL (center-) position 304 with even higher confidence and accuracy in the reference frame 412. This increased accuracy demonstrates the benefit of combining the information captured by the two cross-correlators 301 and 302 separately.

It is noted that the combined cross-correlator 303 in the above described embodiments can be calculated in different ways. A useful approach is to compute it as an element-wise product of the disk cross-correlator 301 and the edge cross-correlator 302. Optionally, the disk cross-correlator 301 and the edge cross-correlator 302 can be weighted differently. This can be achieved, for example, by raising at least one of the two correlation functions 301 and 302 to a power different from 1.

As mentioned, the Image Recognition System 300 can determine the LAL position 304 by determining a position of a maximum of the combined cross-correlator 303. Beyond that, the LAL Tracker 100 can be configured for assigning a confidence indicator CI to the determined LAL position 304 based on a value of the combined cross-correlator 303 corresponding to the maximum. In other embodiments, the curvature of the combined cross-correlator 303, measuring how sharp is the maximum, can be additionally factored into the confidence indicator CI.

Figure 8:
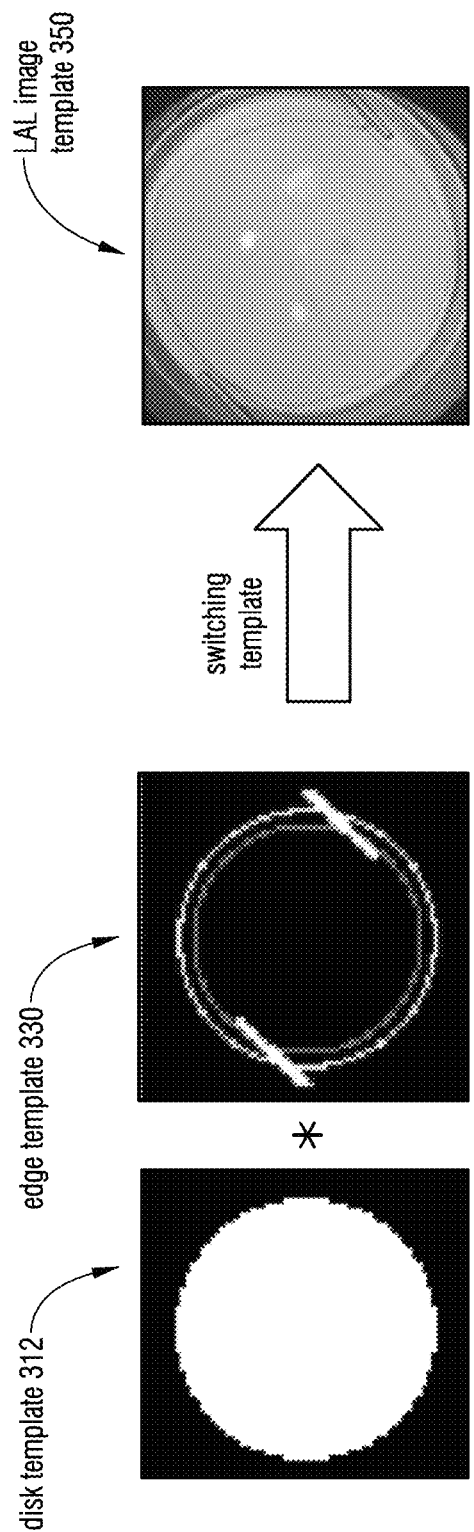
FIG. 8 illustrates switching a template.

FIG. 8 illustrates that at the start of the image recognition process, the confidence indicator CI starts out with low values, since the scanning over the possible shift vectors (m,n) typically starts somewhere away from the maximum of the combined cross-correlator 303 $C_{m,n}$. The confidence indicator CI typically increases as the shift vector (m,n), the relative shift between the LAL image 210 and the disk template 312, and the shift between the LAL gradient image 320 and the edge template 330, is scanned across the search space, and the scanning search finds higher and higher values of the combined cross-correlator 303 $C_{m,n}$. A further factor causing delay is the rotational search of the haptic-edge template 336, with the incremental angle 337-i. As the search process progresses, the confidence indicator CI can increase above a confidence threshold. This threshold can be chosen judiciously, so that once CI exceeds this threshold, the determined LAL position 304 can be trusted.

With today's powerful computers, exceeding this CI threshold can be achieved quite fast. In some relevant embodiments, the combined cross-correlator 303 can rise above a reliable confidence indicator CI in 10-50 ms, in some cases in 20-30 ms. Thus, in embodiments where the video frame time is 50-100 ms, i.e. the frame rate is 10-20 frames/sec, the LAL tracker 100 can determine the LAL position 304 with high confidence for each frame.

Once CI crosses the confidence threshold, and the LAL position 304 is determined with a high confidence indicator CI, a notable improvement of the search process can be implemented. The Image Recognition System 300 can be configured for switching from the disk-template 312 and the edge-template 330 to a LAL image template 350 that is based on the LAL image captured at the maximum of the combined cross-correlator 303 $C_{m,n}$. After this switch to the LAL image template 350, the LAL position 304 can be determined in the subsequent video frames by determining the combined cross-correlator 303 of the LAL image 210 with this captured LAL image template 350. Using such a LAL image template 350 can increase the confidence indicator CI to even higher values.

Figure 9:
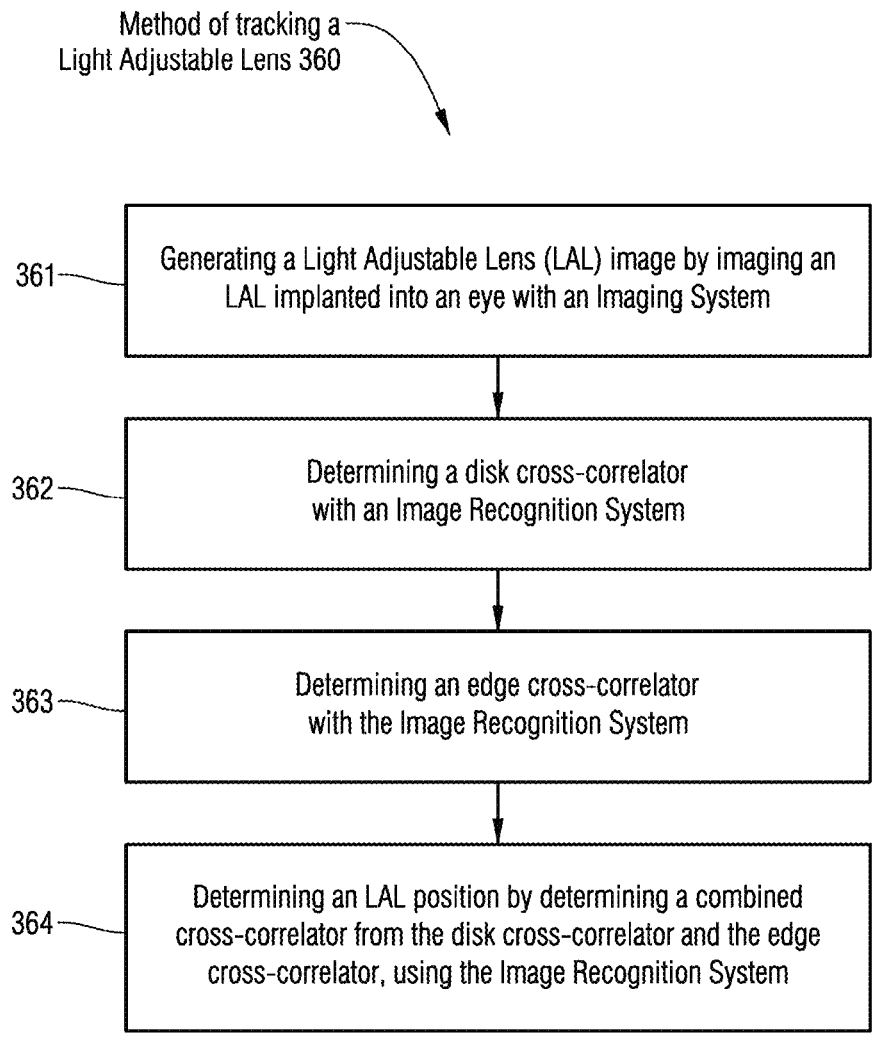
FIG. 9 illustrates a method of tracking a LAL.

The above description characterized the LAL Tracker 100 and a method how it determines the LAL position 304. FIG. 9 summarizes this method 360 for completeness. This method 360 of tracking a Light Adjustable Lens 10 can include:

Generating 361 of the LAL image 210 by imaging the LAL 10 implanted into an eye with the Imaging System 200;

Determining 362 the disk cross-correlator 301 with the Image Recognition System 300;

Determining 363 the edge cross-correlator 302 with the Image Recognition System 300; and Determining 364 the LAL position 304 by determining the combined cross-correlator 303 from the disk cross-correlator 301 and the edge cross-correlator 302, using the Image Recognition System 300.

The method 360 can also include controlling an illumination 540 of the LAL by the Illumination Controller 400 and by the Light Delivery Device 500, based on the determined LAL position 304.

Tracking-Based Illumination Control System

FIGS. 10-14 describe a Tracking-based Illumination Control System 600 and its operations. FIG. 10A illustrates that the LAL Tracker 100 can be coupled to the Illumination Controller 400 that can be configured for receiving the determined LAL position 304, and for generating an illumination control signal 430 based on the received LAL position 304. Further, the Illumination Controller 400 can be coupled to the Light Delivery Device 500 that is configured for receiving the illumination control signal 430 from the Illumination Controller 400, and for illuminating the LAL 10 in relation to the received illumination control signal 430.

The LAL Tracker 100, its Imaging System 200 and Image Recognition System 300 and the Illumination Controller 400 together can be parts of the Tracking-based Illumination Control System 600 as described in more detail next. This Tracking-based Illumination Control System 600 can be comprising: the Light Adjustable Lens (LAL) Tracker 100, for tracking a LAL 10 implanted in an eye, including the Imaging System 200, for creating a LAL image 210 by imaging the LAL 10, and the Image Recognition System 300, coupled to the Imaging System 200, for determining the LAL position 304 in a reference frame 412, based on the LAL image 210 and the combined cross-correlator 303; and the Illumination Controller 400, coupled to the LAL Tracker 100, configured for determining a LAL misalignment factor 420 corresponding to a LAL misalignment 410 that characterizes a misalignment of the LAL position 304 with a LAL illumination pattern 550, and for generating the illumination control signal 430 in relation to the determined LAL misalignment factor 420. In some embodiments of the Tracking-based Illumination Control System 600, the Illumination Controller 400 can be integrated with at least one of the Image Recognition System 300 and the Light Delivery Device 500; in some cases, with both. In some embodiments, the Illumination Controller 400 can send the illumination control signal 430 to the LDD 500, in others, to an operator of the Tracking-based Illumination Control System 600 and the LDD 500, to prompt some kind of action, or a realignment of the LAL position 304 with a LAL illumination pattern 550.

Figure 10A:
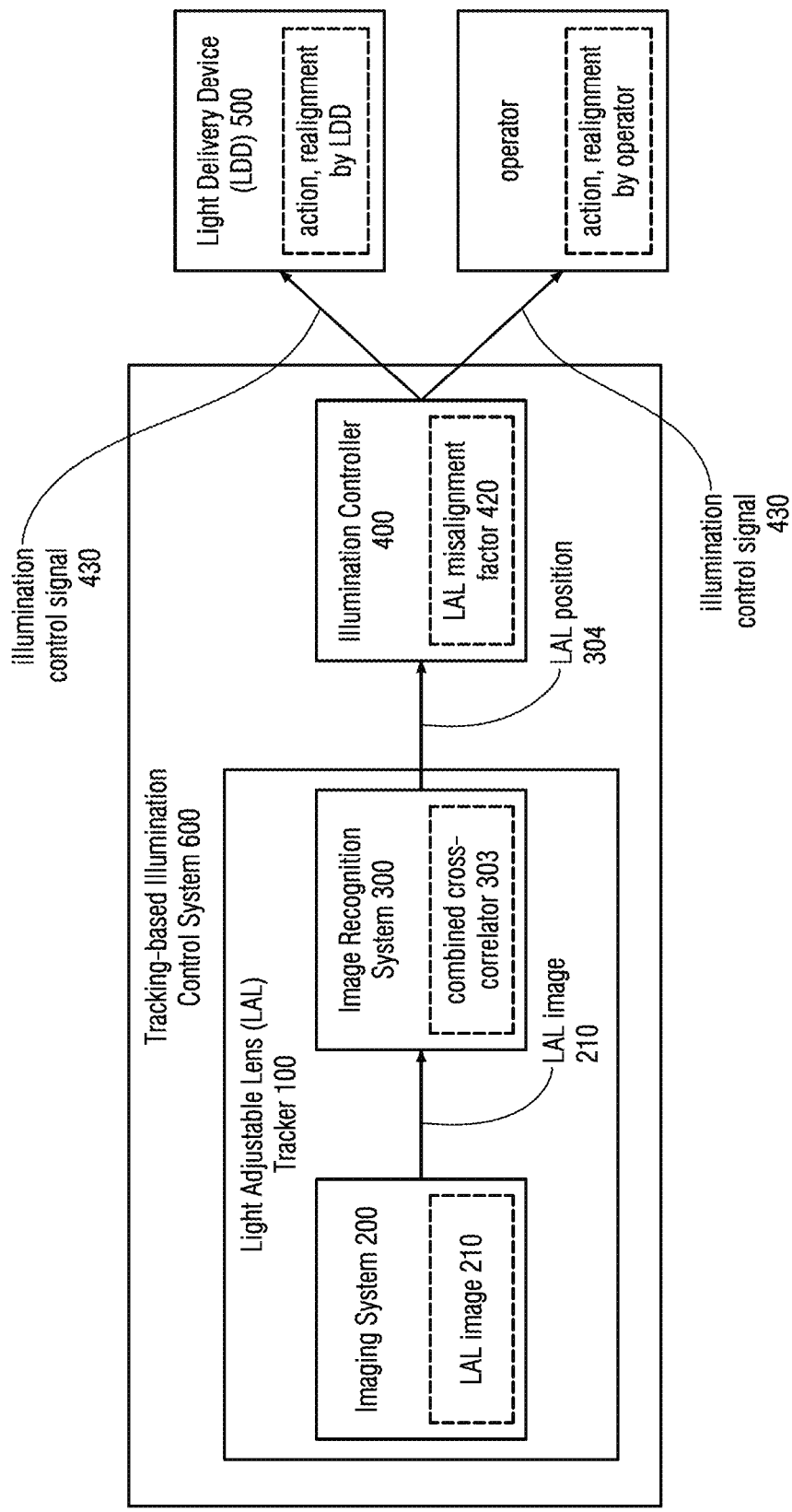
FIGS. 10A-C illustrate a Tracking-based Illumination Control system and a method of its operation.
Figure 10B:
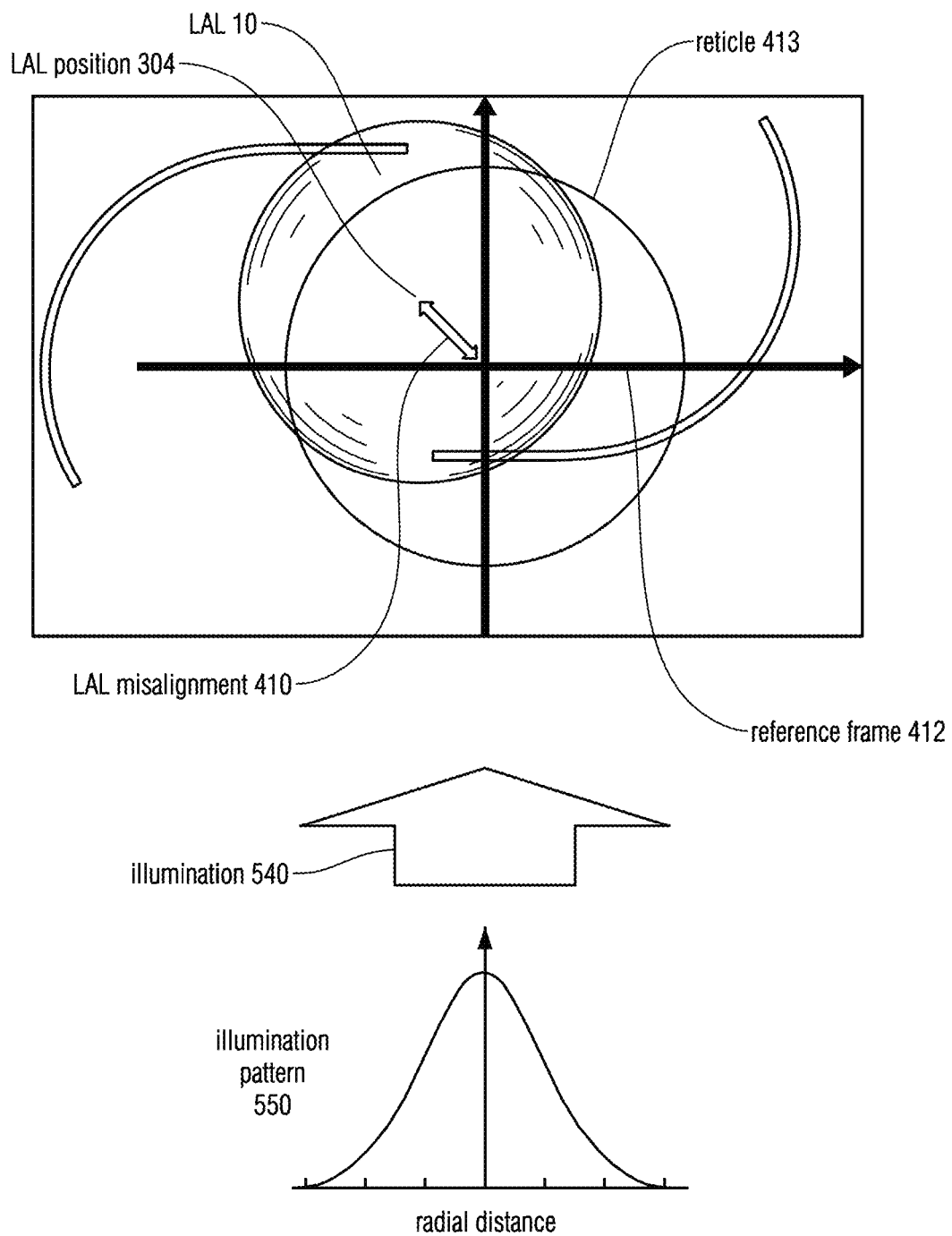

FIG. 10B illustrates a typical case of the LAL misalignment 410. In a typical embodiment, the LAL position 304 within the reference frame 412 can be simply identified as the LAL misalignment 410, since the illumination pattern 550 is typically centered in the reference frame 412. In some embodiments, it may be possible that the illumination pattern 550 is de centered relative to the reference frame 412, or that the optical axis of the Imaging System 200 is not aligned with the reference system 412, or that the imaging System 200 has a partially distinct optical system relative to the LDD 500, and the two are not calibrated together. In these embodiments, the LAL misalignment 410 can be identified as the relative misalignment between the LAL position 304 and the de-center of the illumination pattern 550.

In yet further embodiments, the reference frame 412 can be also referenced to at least one of the Imaging System 200, the Image Recognition System 300, the Illumination Controller 400, and a Light Delivery Device 500, some of which may not be calibrated together. The resulting de-center of the illumination pattern 550 can be used as a correction for the computation of the relation between the LAL position 304 and the LAL misalignment 410. As described before, in the Tracking-based Illumination Control System 600, the reference frame 412 can be represented by a physical reticle 413, a projected reticle 413, or an electronically generated reticle 413.

Figure 10C:
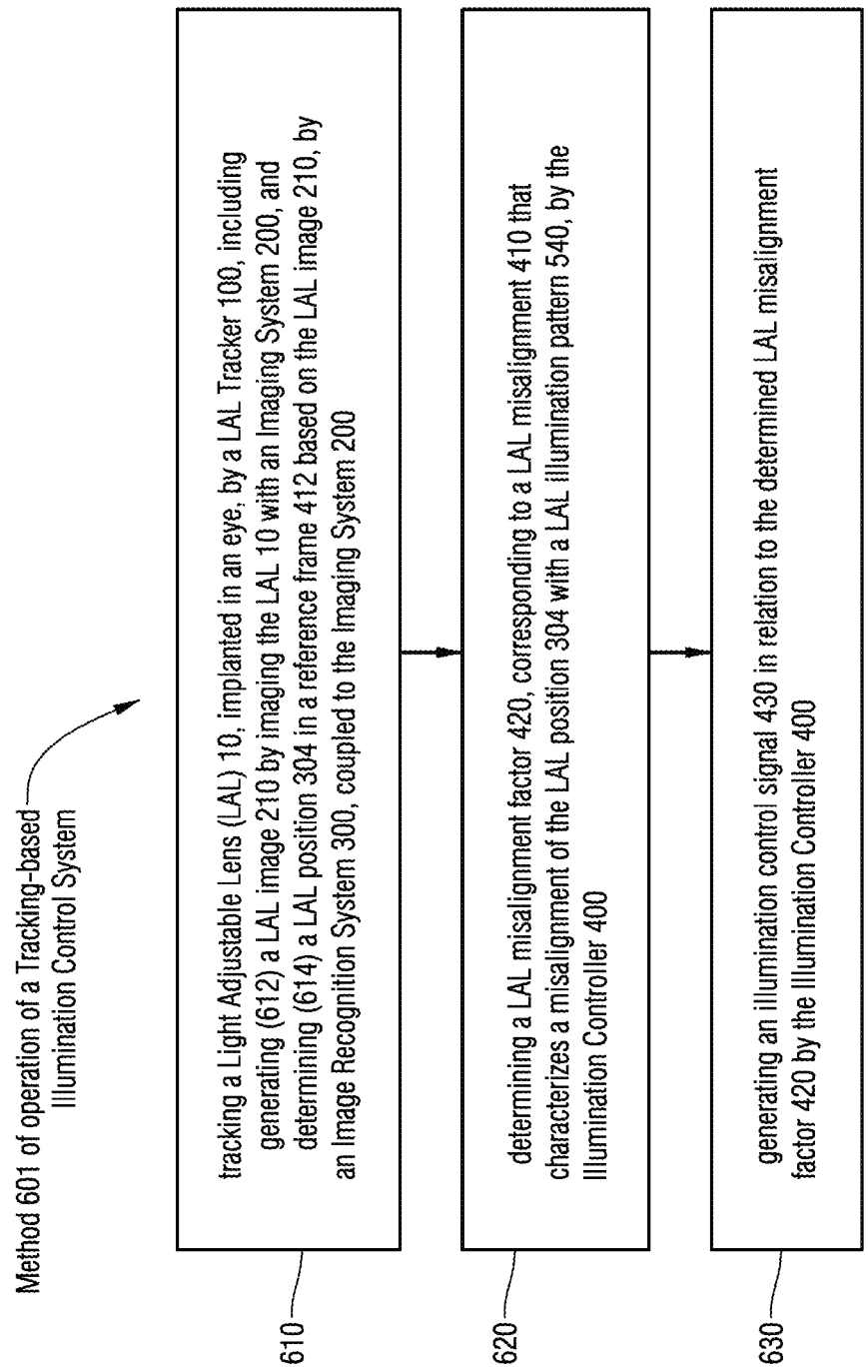

FIG. 10C illustrates a method 601 of operation of the Tracking-based Illumination Control System 600. The method 601 can comprise the steps of:

Tracking 610 a Light Adjustable Lens (LAL) 10, implanted in an eye, by the LAL Tracker 100, including
generating 612 the LAL image 210 by imaging the LAL 10 with the Imaging System 200, and
determining 614 the LAL position 304 based on the LAL image 210 by the Image Recognition System 300, coupled to the Imaging System 200;

Determining 620 the LAL misalignment factor 420, corresponding to the LAL misalignment 410 that characterizes a misalignment of the LAL position 304 with the LAL illumination pattern 550, by the Illumination Controller 400 that is coupled to the LAL Tracker 100; and Generating 630 the illumination control signal 430 in relation to the determined LAL misalignment factor 420 by the Illumination Controller 400.

In embodiments, where the Image Recognition System 400 and the Illumination Controller 400 are at least partially integrated, the determining 614 of the LAL position 304 by the Image Recognition System 400 and the determining 620 of the LAL misalignment factor 420 by the Illumination Controller 400 can be a correspondingly integrated step.

Figure 11A:
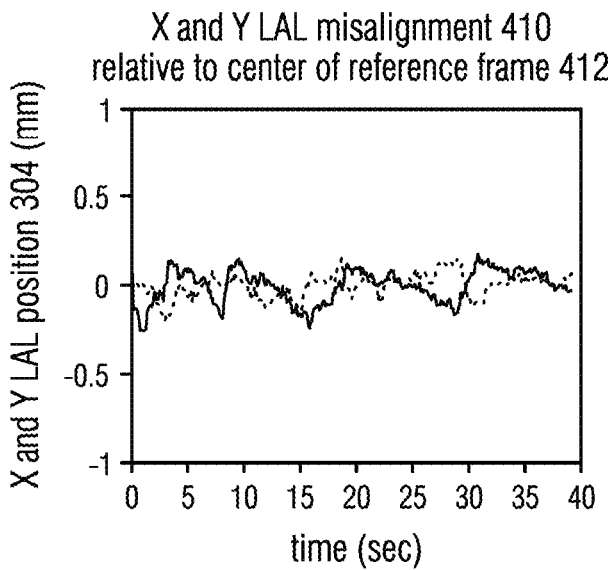
FIGS. 11A-C illustrate several embodiments of the LAL misalignment factor.
Figure 11A:
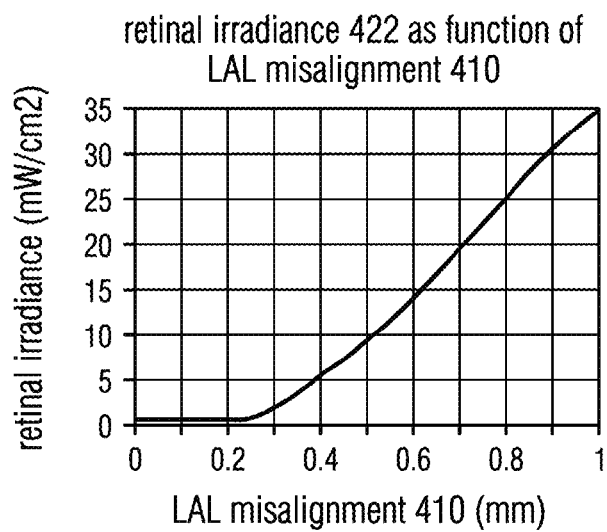
Figure 11A:
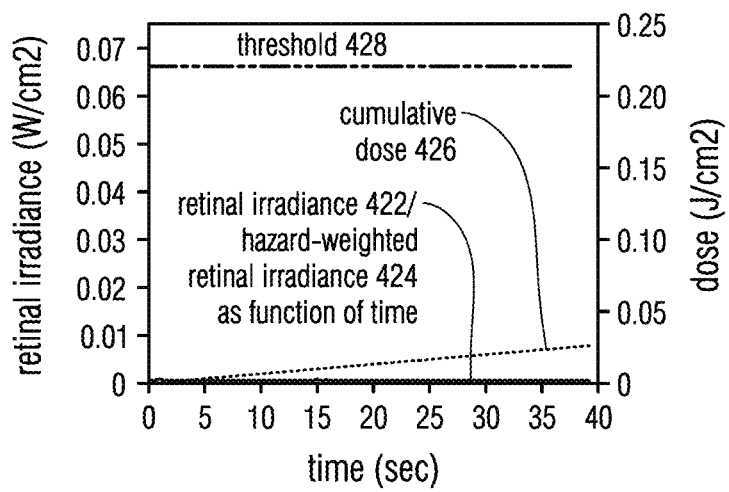
Figure 11B:
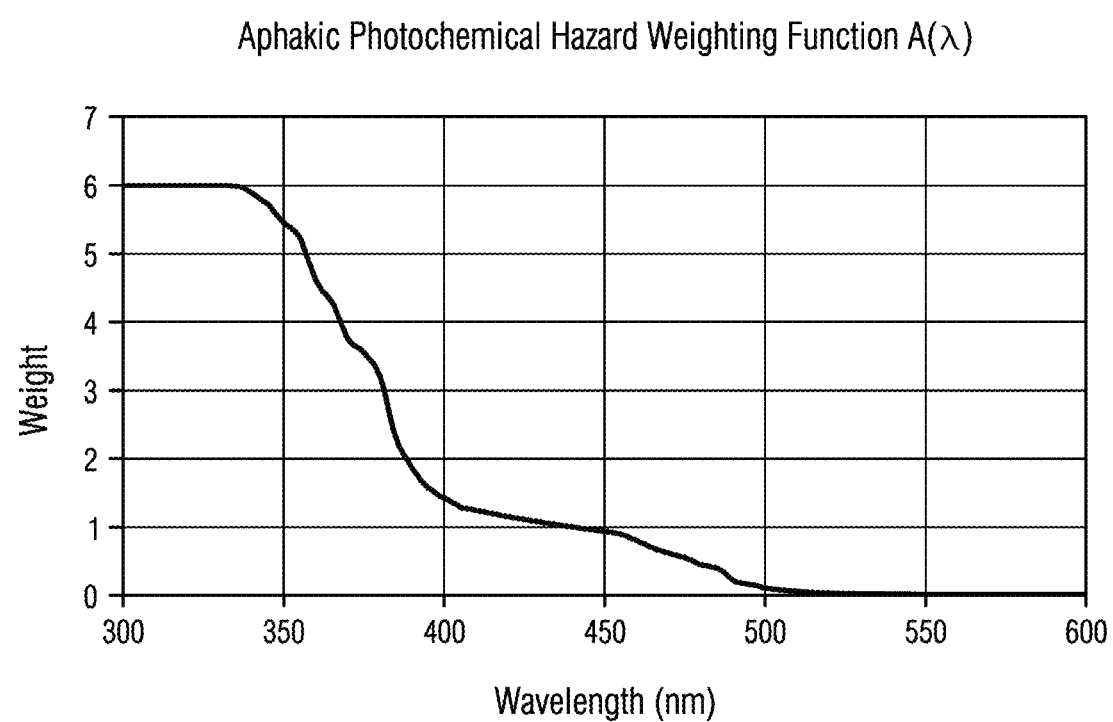
Figure 11C:
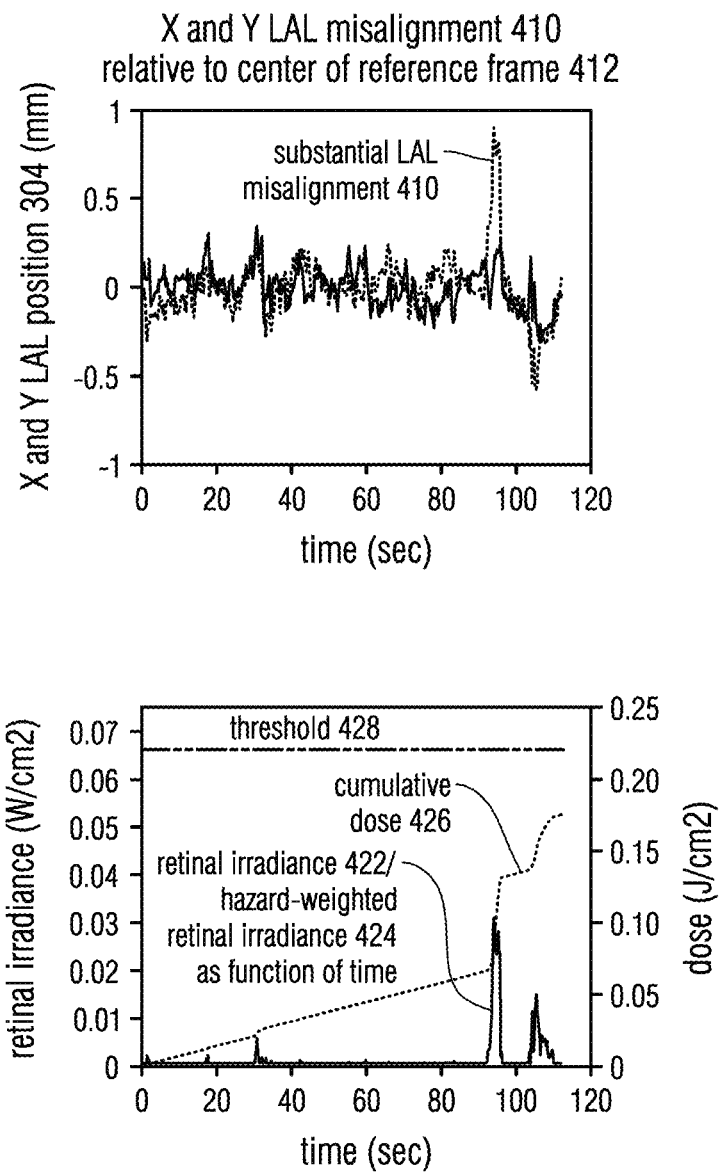

FIGS. 11A-C illustrate the determining 620 of the LAL misalignment factor 420 based on the LAL misalignment 410. In some embodiments, the LAL misalignment factor 420 is simply the LAL misalignment 410; in others, it represents, or converts, the LAL misalignment 410 into a form that captures the medical impact of the LAL misalignment 410 in a medically useful and actionable manner.

In FIG. 11A, the left panel shows the X and Y coordinates of the LAL position 304 as a function of time. (a) In simple embodiments, the LAL misalignment factor 420 can simply be the LAL misalignment 410, as captured by its X and Y coordinates. For example, the LAL misalignment factor 420 can be the magnitude of the LAL misalignment 410. When the illumination pattern 550 is centered in the reference frame 412, the LAL misalignment 410 itself is further simplified into the LAL position 304. When the illumination pattern 550 is de-centered relative to the reference frame 412, then the de-center of the illumination pattern 550 is to be combined with the LAL position 304 to determine the LAL misalignment 410, which can then be identified as the LAL misalignment factor 420.

(b) The central panel of FIG. 11A indicates that a second class of the LAL misalignment factor 420 can be a retinal irradiance 422, the irradiance experienced by the retina during the illumination 540. As long as the LAL 10 is not misaligned with the illumination pattern 550, the retinal irradiance 422 is very small, as the LAL 10 contains a strongly UV absorbing material, as well as a UV absorbing back-layer 19 that attenuate a very high percentage of the incident illumination 540. This class of the LAL misalignment factor 420 captures that when the LAL misalignment 410 increases, the first about 0.20-0.25 mm does not increase the retinal irradiance either because the rim 16 of the LAL 10 still absorbs the misaligned illumination 540. However, once the LAL misalignment 410 exceeds this 0.20-0.25 mm rim-related tolerance, the illumination 540 starts to pass by the illumination-absorbing LAL 10 and propagates to the retina unattenuated, thereby exposing the retina to an increasingly higher irradiance. This poses an increasing impact from a medical standpoint. Thus, choosing the retinal irradiance 422 as the LAL misalignment factor 420 better captures the medical effect of the LAL misalignment 410, as it includes the threshold-like onset of retinal irradiance 422 as a function of the LAL misalignment 410.

(c) FIG. 11B illustrates yet another embodiment. Medical, studies indicate that the impact of two illuminations that have the same radiance, but different wavelengths, can have very different medical impact on the retina. This is largely due to the fact that the photons of the shorter wavelength illumination carry more energy, and thus can impact the chemical bonds of the light-sensitive retina more profoundly. This wavelength-dependence can be captured by an "aphakic photochemical hazard weighting function" $A(\lambda)$, shown in FIG. 11B. As an example, an illumination at a wavelength of $\lambda=350$ nm poses more than 5 times the photochemical hazard than an illumination with the same irradiance at a wavelength of $\lambda=450$ nm. To capture this strong wavelength dependence of the medical impact, an embodiment of the LAL misalignment factor 420 can be a hazard-weighted retinal irradiance 424, that is the retinal irradiance 422 weighted, or multiplied, by the aphakic photochemical hazard weighting function $A(\lambda)$.

(d) The right panel of FIG. 11A shows a fourth embodiment of the LAL misalignment factor 420, a cumulative dose 426. The cumulative dose 426 can be constructed by integrating the retinal irradiance 422, or the hazard-weighted retinal irradiance 424 over the illumination time. This cumulative dose 426 captures not just the momentary retinal irradiance 422, or hazard-weighted retinal irradiance 424, but the cumulative irradiated energy that impacted the retina over the illumination time.

The cumulative dose 426 will be illustrated by comparing two particular illumination procedures. FIG. 11A, left panel illustrates an illumination procedure during which the time dependent LAL misalignment 410 remained limited. The right panel shows that accordingly, the cumulative dose 426 remained below a threshold 428 throughout the entire illumination procedure.

FIG. 11C, left panel illustrates a different illumination procedure during which the time dependent LAL misalignment 410 developed a small misalignment around t~30 sec. and substantial misalignments around t~100 sec. Such substantial misalignments can be caused e.g. by an involuntary movement of the patient's eye, or other effects. The right panel shows that these misalignments induced a small spike around t~30 sec and large spikes before and after t~100 sec in the cumulative dose 426. The described four embodiments (a)-(d) of the LAL misalignment factor 420 all can be used to characterize the LAL misalignment 410.

In any of the embodiments (a)-(d), one role of the LAL misalignment factor 420 is to indicate if an undesirable level of the LAL misalignment 410 developed between the LAL 10 and the illumination pattern 550. Should the LAL misalignment factor 420 indicate such an undesirable level of the LAL misalignment 410, the Illumination Controller 400 can generate a corrective illumination control signal 430. This illumination control signal 430 can be directed to the physician operating the LDD 500, or toward the Light Delivery Device 500. For example, in embodiment (d), as shown in the right panel of FIG. 11C, once the cumulative dose 426 reaches the threshold 428, the Illumination Controller 400 can generate a responsive illumination control signal 430. In embodiment (a), where the LAL misalignment factor 420 is simply the LAL misalignment 410, the illumination control signal 430 can be generated when the LAL misalignment 410 exceeds a corresponding threshold. In embodiment (b), where the LAL misalignment factor 420 is the retinal irradiance 422, then the illumination control signal 430 can be generated when the retinal irradiance 422 exceeds a threshold. And in embodiment (c), the illumination control signal 430 can be generated, when the hazard-weighted retinal irradiance 424 exceeds a threshold.

Figure 12A:
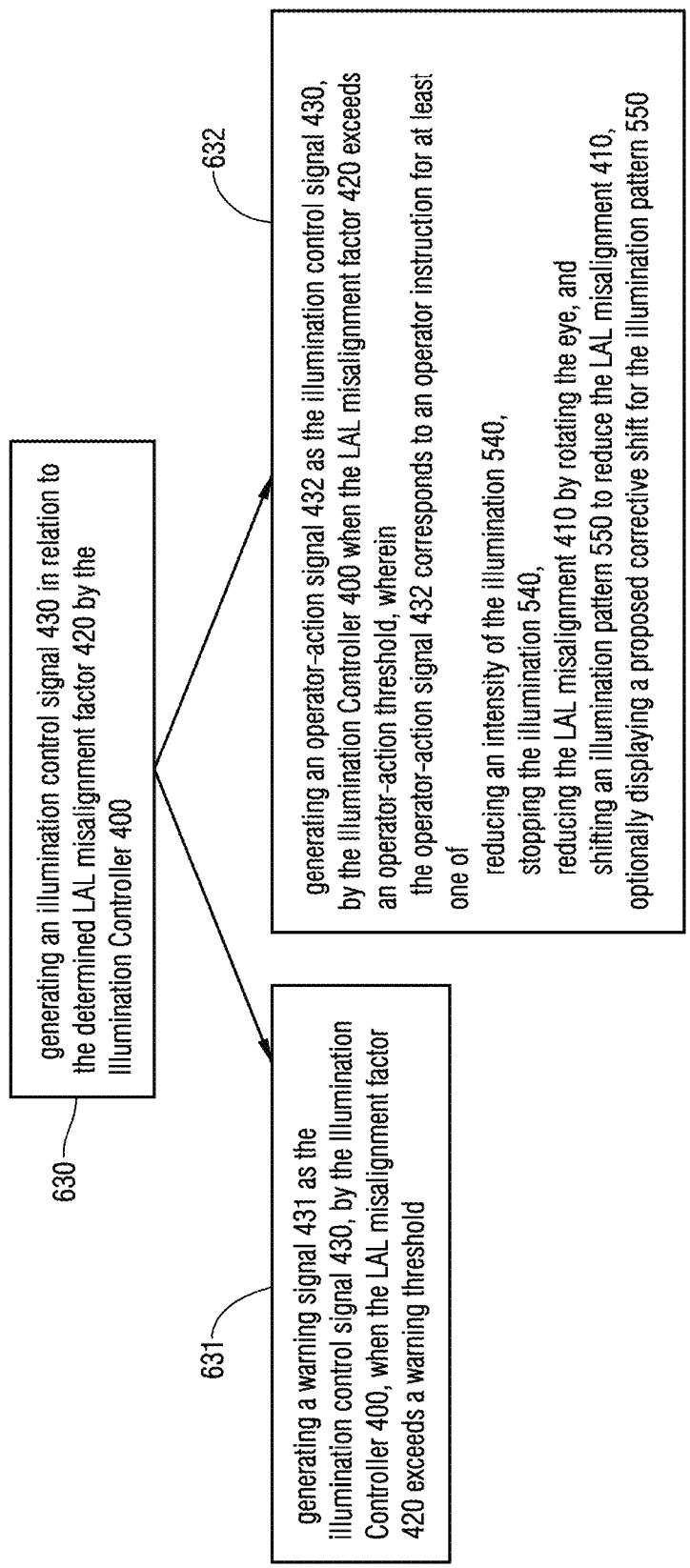
FIGS. 12A-B illustrate embodiments of an illumination control signal.
Figure 12B:
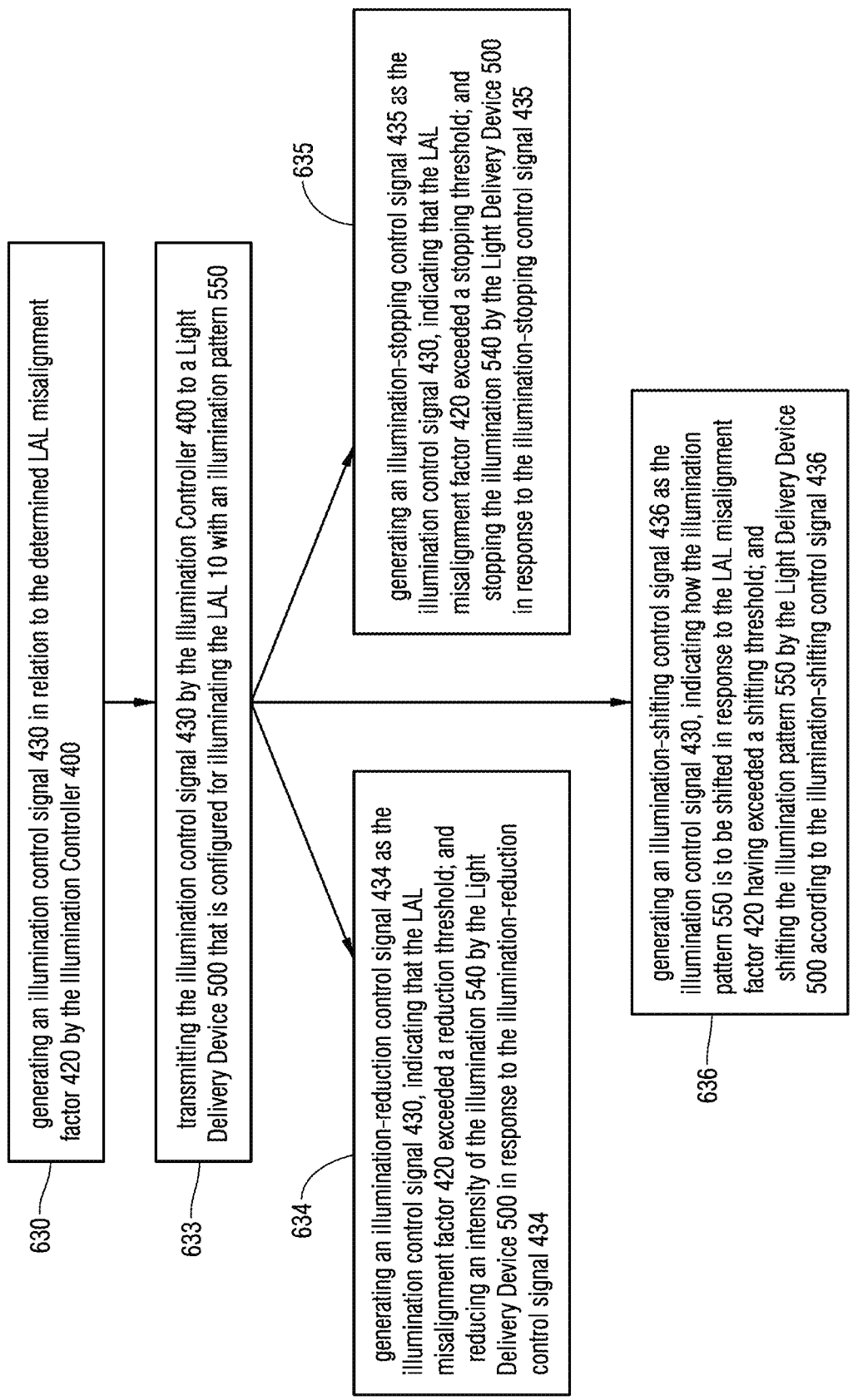

FIGS. 12A-B show that in the generating step 630 of the method 601 in FIG. 10C, the Illumination Controller 400 can be configured for generating the illumination control signal 430 in response to the determined LAL misalignment factor 420 exceeding a threshold. In other embodiments, a smoother ramp can be used instead of the sharp threshold. For example, the illumination control signal 430 can track, or be proportional to the LAL misalignment factor 420.

FIG. 12A illustrates embodiments, when the illumination control signal 430 is sent by the Illumination Controller 400 to an operator of the LDD 500 or the Tracking-based Illumination Control System 600. FIG. 12B illustrates embodiments, when the illumination control signal 430 is sent by the Illumination Controller 400 to the LDD 500.

FIG. 12A shows that the generating the illumination control signal 430 can have many different embodiments. In a step 631, the threshold is a warning threshold and the illumination control signal 430 is a warning signal 431, generated by the Illumination Controller 400 when the LAL misalignment factor 420 exceeds the warning threshold. The warning signal 431 can be generated by at least one of a haptic alarm, an audio alarm, a video alarm, a temperature alarm, a vibrating alarm, and a mechanical alarm for the system operator, typically a physician. For example, in an embodiment where the LAL misalignment factor 420 is the cumulative dose 426, if during an illumination procedure the cumulative dose 426 exceeds the (warning) threshold 428, then the Illumination Controller 400 can generate an audio alarm or a vibrating alarm as the warning signal 431 for the operating physician to prompt a corrective action.

In a step 632, the threshold can be an operator-action threshold and the illumination control signal 430 can be an operator-action signal 432, generated by the Illumination Controller 400, when the LAL misalignment factor 420 exceeds the operator-action threshold. In these embodiments, the operator-action signal 432 can correspond to an operator instruction for at least one of reducing an intensity of the illumination 540, stopping the illumination 540, reducing the LAL misalignment 410 by rotating the eye; or shifting the illumination pattern 550 to reduce the LAL misalignment 410. For example, the operator-action signal 432 can be a visual operator instruction to stop the illumination because the cumulative dose 426 exceeded its threshold 428. Optionally, the operator instruction can also involve displaying a proposed corrective shift for the illumination pattern 550 of the LDD; in other cases, a proposed rotation of the eye.

FIG. 12B shows that some embodiments of the generating step 630 can include step 633, where the Illumination Controller 400 can be configured for transmitting the illumination control signal 430 to the Light Delivery Device 500 that is configured for illuminating the LAL 10 with the illumination pattern 550. In these embodiments, the corrective action can be carried out by the LDD 500, under the control of the operating physician.

In a step 634, the threshold can be a reduction threshold and the illumination control signal 430 can be an illumination-reduction control signal 434, indicating that the LAL misalignment factor 420 exceeded a reduction threshold. In these embodiments, instead of prompting the operator for a responsive action, the Light Delivery Device 500 itself can be configured for reducing an intensity of the illumination 540 in response to the illumination-reduction control signal 434, possibly under the control of the operator.

In a step 635, the threshold can be a stopping threshold and the illumination control signal 430 can be an illumination-stopping control signal 435, indicating that the LAL misalignment factor 420 exceeded the stopping threshold; and the Light Delivery Device 500 can be configured for stopping the illumination 540 in response to the illumination-stopping control signal 435, optionally under the control of the operating physician.

In yet other embodiments, e.g., in step 636, the threshold can be a shifting threshold and the illumination control signal 430 can be an illumination-shifting control signal 436, indicating how the illumination pattern 550 is to be shifted in response to the LAL misalignment factor 420 having exceeded the shifting threshold; and the Light Delivery Device 500 can be configured for shifting the illumination pattern 550 according to the illumination-shifting control signal 436.

Figure 13:
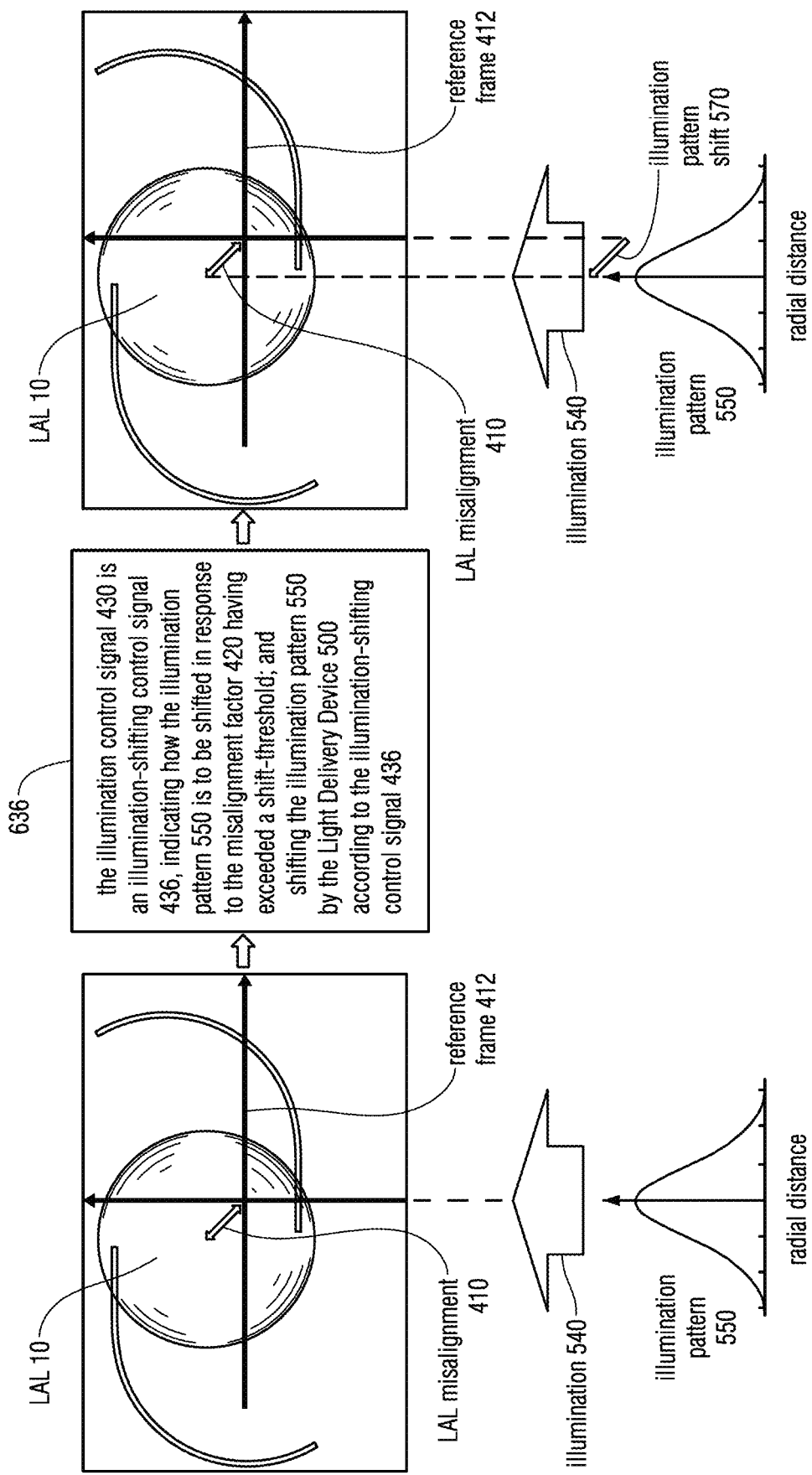
FIG. 13 illustrates an illumination-shifting, control signal.

FIG. 13 illustrates this step 636 is some detail. The left panel describes an embodiment where the illumination pattern 550 is centered relative to the reference frame 412. The LAL Tracker 100 can determine the continuously changing LAL position 304 in real time and forward it to the Illumination Controller 400. Once the LDD 500 started the illumination of the LAL, the Illumination Controller 400 can determine the time-dependent LAL misalignment factor 420 from the LAL position 304, which in the present case can be the cumulative dose 426. At time t, shown in FIG. 13, a shift of the LAL 10 induced a LAL misalignment 410, and the Illumination Controller 400 records a rapidly rising cumulative dose 426. Once this cumulative dose 426 exceeds a shifting threshold, the Illumination Controller 400 sends an illumination-shifting control signal 436 to the LDD 500. This illumination-shifting control signal 436 can include a warning signal to the physician, and a suggested illumination pattern shift 570 for the LDD 500. Optionally, the illumination control signal 430 can also include an illumination-stopping signal 435. Based on the calculations of the Illumination Controller 400, if the LDD 500 itself shifts the illumination pattern 550 with this suggested illumination pattern shift 570, the LAL misalignment factor 420 can be brought under control, and the cumulative dose 426 will stop rising further. Once the physician authorizes the proposed illumination pattern shift 570, the LDD 500 can execute the proposed illumination pattern shift 570. In some cases, there can be a coordinated response: the physician can rotate the eye and the LDD 500 can simultaneously shift the illumination pattern 550, and these two simultaneous actions together can execute the proposes illumination pattern shift 570. Once the proposed illumination pattern shift 570 has been executed, the LDD 500 can continue or resume the illumination. What was just described for this specific case of step 636 can be implemented in many other embodiments.

In embodiments, where the illumination control signal 430 includes an illumination-stopping signal 435, the Tracking-based Illumination Control System 600 can also be configured for determining that the LAL misalignment factor 420 has been reduced below a resume-illumination threshold in response to a preceding illumination control signal 430; and for generating an illumination-resume control signal in relation to the reduced LAL misalignment factor 420.

In the embodiments, where the LDD 500 stops the illumination 540 while the LAL misalignment 410 is reduced, the cumulative dose 426 may be integrated only over the time when the LDD illumination 540 is actually applied. Accordingly, the integration time can be interrupted.

Returning to FIG. 10C and FIG. 12A, in the method 601 of operating the Tracking-based Illumination Control System 600, the generating 630 can comprise the step 631 of generating a warning signal 431 as the illumination control signal 430 by the Illumination Controller 400, when the LAL misalignment factor 420 exceeds a warning threshold.

In other embodiments, the generating 630 can comprise the step 632 of generating an operator-action signal 432 as the illumination control signal 430 by the Illumination Controller 400, when the LAL misalignment factor 420 exceeds an operator-action threshold, wherein the operator-action signal 432 corresponds to an operator instruction for at least one of reducing an intensity of the illumination 540, stopping the illumination 540, reducing the LAL misalignment 410 by rotating the eye; and shifting the illumination pattern 550 to reduce the LAL misalignment 410, optionally displaying a proposed corrective shift for the illumination pattern 550.

FIG. 12B shows that in some embodiments, the generating 630 can comprise the step 633 of transmitting the illumination control signal 430 by the Illumination Controller 400 to the Light Delivery Device 500 that is configured for illuminating the LAL 10 with the illumination pattern 550.

In some embodiments, the generating 630 can comprise the step 634 of generating an illumination-reduction control signal 434 as the illumination control signal 430, indicating that the LAL misalignment factor 420 exceeded a reduction threshold. This can be followed by reducing an intensity of the LAL illumination 540 by the Light Delivery Device 500 in response to the illumination-reduction control signal 434.

In some embodiments, the generating 630 can comprise the step 635 of generating an illumination-stopping control signal 435 as the illumination control signal 430, indicating that the LAL misalignment factor 420 exceeded a stopping threshold. This can be followed by stopping the LAL illumination 540 by the Light Delivery Device 500 in response to the illumination-stopping control signal 435.

In some embodiments, the generating 630 can comprise the step 636 of generating an illumination-shifting control signal 436 as the illumination control signal 430, indicating how the illumination pattern 550 is to be shifted in response to the LAL misalignment factor 420 having exceeded a shift-threshold. This can be followed by shifting the illumination pattern 550 according to the illumination-shifting control signal 436 by the Light Delivery Device 500 to reduce the LAL misalignment 410.

Figure 14:
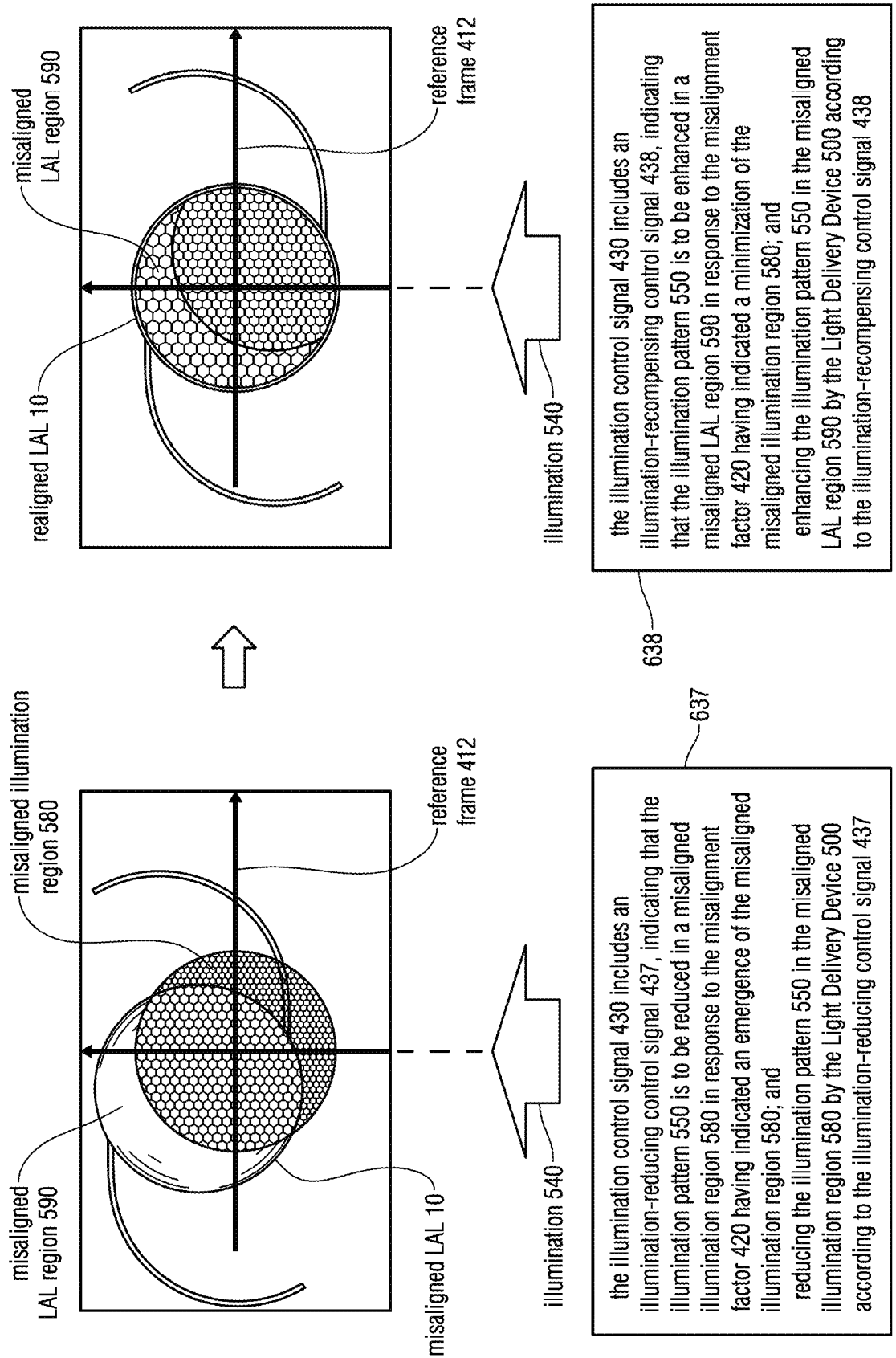
FIG. 14 illustrates an illumination-reducing and an illumination-recompensing control signal.

FIG. 14 illustrates yet another embodiment of the Tracking-based Illumination Control System 600. When the LAL 10 gets misaligned with the illumination pattern 550, the misalignment factor 420 can indicate that a misaligned illumination region 580 emerged. The illumination 540 could potentially pass by the LAL 10 in this misaligned illumination region 580, possibly causing an undesired outcome. The misalignment factor 420 indication can cause the Illumination Controller 400 to generate an illumination-reducing control signal 437 as part of the illumination control signal 430, to indicate that the illumination pattern 550 is to be reduced, or stopped, in the misaligned illumination region 580, to avoid the illumination 540 pass by the LAL 10. In response to this, the Light Delivery Device 500 can reduce, or stop, the illumination pattern 550 in the misaligned illumination region 580 according to the illumination-reducing control signal 437, preventing the undesired outcome.

Another consequence of the LAL misalignment is that a misaligned LAL region 590 emerges on the side of the LAL 10 that is complementary to the misaligned illumination region 580. This misaligned LAL region 590 is outside the illumination pattern 550. For the time period of the misalignment, this misaligned LAL region 590 does not receive its assigned illumination pattern 550, and therefore, its refractive properties are adjusted insufficiently by the illumination 540. The refractive properties of the LAL 10 in the misaligned LAL region 590 are adjusted to a lesser degree than the doctor planned. Next, steps of a method will be described to compensate for this insufficient illumination of the misaligned LAL region 590.

Once, in response to the illumination control signal 430, the doctor or the LDD 500 realigns the LAL 10 approximately, or completely, with the illumination pattern 550, and accordingly the misaligned illumination region 580 gets minimized, or eliminated, the Illumination Controller 400 can generate an illumination-recompensing control signal 438, indicating that the illumination pattern 550 is to be enhanced in the misaligned LAL region 590. This step is performed in order to the Light Delivery Device 500 to enhance the illumination pattern 550 in the misaligned LAL region 590 according to the illumination-recompensing control signal.

Summarizing the above in terms of method steps, the method 601 can include

- Generating 637 the illumination-reducing control signal 437 as part of the illumination control signal 430, indicating that the illumination pattern 550 is to be reduced in the misaligned illumination region 580, in response to the misalignment factor 420 having indicated an emergence of the misaligned illumination region 580;
- Reducing the illumination pattern 550 in the misaligned illumination region 580 according to the illumination-reducing control signal 437 by the Light Delivery Device 500;
- Generating 638 the illumination-recompensing control signal 438 as part of the illumination control signal 430, indicating that the illumination pattern 550 is to be enhanced in the misaligned LAL region 590, in response to the misalignment factor 420 having indicated a minimization of the misaligned illumination region 580; and Enhancing the illumination pattern 550 in the misaligned LAL region 590 by the Light Delivery Device 500 according to the illumination-recompensing control signal 438.

Various eye-tracking systems are known in the art. Some of them are used in conjunction with systems that illuminate an eye, such as Avedro's corneal cross-linking illumination system. Such existing systems and procedures typically image the iris or the limbus, and illuminate the cornea using this imaging. It is preferred that the illumination hits only the iris after traversing the cornea, instead of the illumination entering the pupil, because then it would impact the retina. There are substantial differences between embodiments of the here-described systems 100 and 600, and existing systems, such as Avedro's.

(a) Existing systems track living ophthalmic tissue, such as the iris or the limbus, whereas systems 100/600 track an implanted device, a LAL 10. This difference has several consequences. For example, the LAL is transparent, in contrast to the non-transparent iris and limbus. Therefore, it is much harder to image the transparent LAL with the same resolution as the iris or the limbus.

(b) The natural lens of the eye is strongly absorbing in the UV. Therefore, if a UV illumination by an existing system, directed at the iris, gets misaligned and partially passes into the eye through the pupil, the natural lens will absorb it and it does not reach the retina. Thus, the occasional illumination misalignment means a very limited problem, and correspondingly, the precision of these systems can be low, tolerating misalignments larger than 1 mm, 2 mm, or higher. In contrast, the LDD 500 illuminates the eye with the natural lens removed. In this case, when the illumination pattern 550 is misaligned with the UV absorbing LAL 10, the portion of the illumination 540 that passes by the LAL 10 can impact the retina unattenuated. Therefore, the precision of the illumination pattern 550 of the LDD 500 needs to be much higher. In embodiments, where the LAL misalignment factor 420 is the LAL misalignment 410, in the here-described higher-precision LAL Tracker 100 and Tracking-based Illumination Control System 600, an illumination control signal 430 can already be generated when the LAL misalignment 410 exceeds 1.0 mm, in other embodiments, when it exceeds 0.8 mm, 0.6 mm, 0.4 mm, or 0.2 mm. In embodiments, where the LAL misalignment factor 420 is the optionally hazard-weighted cumulative dose 426, an illumination control signal 430 can be already generated when the optionally hazard-weighted cumulative dose 426 exceeds 1.0 $J/cm^2$, 0.5 $J/cm^2$, or 0.25 $J/cm^2$.

(c) Another related consideration is that the corneal crosslinking procedures are typically performed with a non-dilated iris or pupil, with a typical diameter 2.5-4 mm, while the diameter of the natural lens grows over the lifetime and can reach 10 mm. Thus, the misaligned illumination that passes through the pupil is largely blocked by the natural lens, preventing it from proceeding towards the retina. In contrast, the LAL illumination is often performed with a dilated iris, with typical diameter of more than 5, 6, or 7 mm. Since the diameter of the LAL 10 can be 5-6 mm, a substantially misaligned illumination 540 can bypass the LAL 10 through a several $mm^2$ area to propagate toward the retina. The difference in the pupil being dilated or not is another reason why a much higher precision is expected from the LAL Tracker 100 and Tracking-based Illumination Control System 600.

(d) Finally, some corneal crosslinking illumination techniques seem to use limited power, as they seek to modify sensitive ocular tissue. In some cases, the illumination power density seems to be a few $mW/cm^2$, such as 3 $mW/cm^2$. In contrast, the illumination 540 by the LDD 500 seeks to modify the implanted LAL 10, and thus can have a power density of hundreds of $mW/cm^2$. In some embodiments, this power density can be higher than 300 $mW/cm^2$, in some cases higher than 500 $mW/cm^2$, in some cases higher than 700 $mW/cm^2$. This much higher illumination power density is yet another motivation for making the LAL Tracker 100 and Tracking-based Illumination Control System 600 much more precise. Re-expressing this difference in total doses applied to the eye, existing systems seem to apply a total dose around 5 $J/cm^2$. In contrast, the illumination 540 from the LDD 500 can apply a total energy density, or dose, higher than 30 $J/cm^2$, in some cases higher than 50 $J/cm^2$, in yet other embodiments, higher than 70 $J/cm^2$. As before, the higher dose is applied to the eye, the higher precision is expected from the system to limit even the potential dose hitting the retina to very small values.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A Tracking-based Illumination Control System, comprising:
    a Light Adjustable Lens (LAL) Tracker for tracking a LAL implanted in an eye, including
        an Imaging System, for creating a LAL image by imaging the LAL, and
        an Image Recognition System, coupled to the Imaging System, for determining a LAL position in a reference frame based on the LAL image; and
    an Illumination Controller, coupled to the LAL Tracker, configured for
    determining a LAL misalignment factor, corresponding to a LAL misalignment that characterizes a misalignment of the LAL position with a LAL illumination pattern, wherein
        the LAL misalignment factor is a cumulative dose, corresponding to an optionally hazard-weighted retinal irradiance, integrated over an illumination time, and
    generating an illumination control signal in relation to the determined LAL misalignment factor.

2. The Tracking-based Illumination Control System of claim 1, wherein:
    the Illumination Controller is integrated with at least one of the Image Recognition System and a Light Delivery Device.

3. The Tracking-based Illumination Control System of claim 1, wherein:
the reference frame is referenced to at least one of the Imaging System, the Image Recognition System, the Illumination Controller, and a Light Delivery Device.

4. The Tracking-based Illumination Control System of claim 1, wherein:
an illumination pattern of a Light Delivery Device is centered in the reference frame.

5. The Tracking-based Illumination Control System of claim 1, wherein:
the reference frame includes one of a reticle coupled into the optical system of the Light Delivery Device, and a reticle electronically generated in one of the LAL Tracker and the Illumination Controller.

6. The Tracking-based Illumination Control System of claim 1, wherein:
the LAL misalignment factor is one of the LAL misalignment, a retinal irradiance, and a hazard-weighted retinal irradiance.

7. The Tracking-based Illumination Control System of claim 1, wherein:
the Illumination Controller is configured for generating the illumination control signal in response to the determined LAL misalignment factor exceeding a threshold.

8. The Tracking-based Illumination Control System of claim 7, wherein:
the threshold is a warning threshold and the illumination control signal is a warning signal, generated by the Illumination Controller when the LAL misalignment factor exceeds the warning threshold.

9. The Tracking-based Illumination Control System of claim 8, wherein:
the warning signal is generated by at least one of a haptic alarm, an audio alarm, a video alarm, a temperature alarm, a vibrating alarm, and a mechanical alarm.

10. The Tracking-based Illumination Control System of claim 7, wherein:
the threshold is an operator-action threshold and the illumination control signal is an operator-action signal, generated by the Illumination Controller when the LAL misalignment factor exceeds the operator-action threshold, wherein
the operator-action signal corresponds to an operator instruction for at least one of
reducing an intensity of an illumination,
stopping the illumination,
reducing the LAL misalignment by rotating the eye; and
shifting an illumination pattern to reduce the LAL misalignment, optionally displaying a proposed corrective shift for the illumination pattern.

11. The Tracking-based Illumination Control System of claim 7, wherein:
the Illumination Controller is configured for transmitting the illumination control signal to a Light Delivery Device that is configured for illuminating the LAL with an illumination pattern.

12. The Tracking-based Illumination Control System of claim 11, wherein:
the threshold is a reduction threshold and the illumination control signal is an illumination-reduction control signal, indicating that the LAL misalignment factor exceeded the reduction threshold; and
the Light Delivery Device is configured for reducing an intensity of the illumination in response to the illumination-reduction control signal.

13. The Tracking-based Illumination Control System of claim 11, wherein:
the threshold is a stopping threshold and the illumination control signal is an illumination-stopping control signal, indicating that the LAL misalignment factor exceeded the stopping threshold; and
the Light Delivery Device is configured for stopping the illumination in response to the illumination-stopping control signal.

14. The Tracking-based Illumination Control System of claim 11, wherein:
the threshold is a shifting threshold and the illumination control signal is an illumination-shifting control signal, indicating how an illumination pattern is to be shifted in response to the LAL misalignment factor having exceeded the shifting threshold; and
the Light Delivery Device is configured for shifting the illumination pattern according to the illumination-shifting control signal.

15. The Tracking-based Illumination Control System of claim 11, wherein:
the illumination control signal includes an illumination-reducing control signal, indicating that the illumination pattern is to be reduced in a misaligned illumination region in response to the misalignment factor having indicated an emergence of the misaligned illumination region;
the Light Delivery Device is configured for reducing the illumination pattern in the misaligned illumination region according to the illumination-reducing control signal;
the illumination control signal includes an illumination-recompensing control signal, indicating that the illumination pattern is to be enhanced in a misaligned LAL region in response to the misalignment factor having indicated a minimization of the misaligned illumination region; and
the Light Delivery Device is configured for enhancing the illumination pattern in the misaligned LAL region by the Light Delivery Device according to the illumination-recompensing control signal.

16. A method of operation of a Tracking-based Illumination Control System, the method comprising the steps of:
tracking a Light Adjustable Lens (LAL), implanted in an eye, by a LAL Tracker, including
creating a LAL image by imaging the LAL with an Imaging System, and
determining a LAL position based on the LAL image by an Image Recognition System, coupled to the Imaging System;
determining a LAL misalignment factor, corresponding to a LAL misalignment that characterizes a misalignment of the LAL position with a LAL illumination pattern, by an Illumination Controller, coupled to the LAL Tracker, wherein the LAL misalignment factor is a cumulative dose, corresponding to a retinal irradiance integrated over an illumination time; and
generating an illumination control signal in relation to the determined LAL misalignment factor by the Illumination Controller.

17. The method of claim 16, wherein:
the Image Recognition System and the Illumination Controller are integrated; and
the determining the LAL position by the Image Recognition System and the determining the LAL misalignment by the Illumination Controller is a correspondingly integrated step.

18. The method of claim 16, the generating comprising:
generating a warning signal as the illumination control signal by the Illumination Controller when the LAL misalignment factor exceeds a warning threshold.

19. The method of claim 16, the generating comprising:
generating an operator-action signal as the illumination control signal by the Illumination Controller, when the LAL misalignment factor exceeds an operator-action threshold, wherein
the operator-action signal corresponds to an operator instruction for at least one of
  reducing an intensity of an illumination,
  stopping the illumination,
  reducing the LAL misalignment by rotating the eye; and
  shifting the LAL illumination pattern to reduce the LAL misalignment, optionally displaying a proposed shift for the LAL illumination pattern.

20. The method of claim 16, comprising:
transmitting the illumination control signal by the Illumination Controller to a Light Delivery Device that is configured for illuminating the LAL with the LAL illumination pattern, impacted by the illumination control signal.

21. The method of claim 20, comprising:
generating an illumination-stopping control signal as the illumination control signal, indicating that the LAL misalignment factor exceeded a stopping threshold; and
stopping the LAL illumination by the Light Delivery Device in response to the illumination-stopping control signal.

22. The method of claim 20, comprising:
generating an illumination-shifting control signal as the illumination control signal, indicating how the LAL illumination pattern is to be shifted in response to the LAL misalignment factor having exceeded a shift-threshold; and
shifting the LAL illumination pattern according to the illumination-shifting control signal by the Light Delivery Device to reduce the LAL misalignment.

23. The method of claim 20, comprising:
generating an illumination-reducing control signal as part of the illumination control signal, indicating that the illumination pattern is to be reduced in a misaligned illumination region, in response to the misalignment factor having indicated an emergence of the misaligned illumination region;
reducing the illumination pattern in the misaligned illumination region according to the illumination-reducing control signal by the Light Delivery Device;
generating an illumination-recompensing control signal as part of the illumination control signal, indicating that the illumination pattern is to be enhanced in a misaligned LAL region in response to the misalignment factor having indicated a minimization of the misaligned illumination region; and
enhancing the illumination pattern in the misaligned LAL region by the Light Delivery Device according to the illumination-recompensing control signal.

* * * * *